(12) United States Patent
Hagen et al.

(10) Patent No.: US 12,727,918 B2
(45) Date of Patent: Sep. 8, 2026

(54) IMPLANT FOR FIXING A CRANIAL BONE FLAP IN A CRANIAL OPENING

(71) Applicant: Aesculap AG, Tuttlingen (DE)

(72) Inventors: Thomas Hagen, Tuttlingen (DE); Jana Kuemmerlin, Regensburg (DE); Erick Drost, Oberndorf a.N. (DE); Jakob Onken, Mainz (DE); Martin Nonnenmann, Wurmlingen (DE); Tina Dekold, Rottweil (DE); Thomas Pleil, Bad Duerrheim (DE)

(73) Assignee: Aesculap AG, Tuttlingen (DE)

( * ) Notice: Subject to any disclaimer, the term of this patent is extended or adjusted under 35 U.S.C. 154(b) by 0 days.

(21) Appl. No.: 18/841,806

(22) PCT Filed: Feb. 6, 2023

(86) PCT No.: PCT/EP2023/052850
§ 371 (c)(1),
(2) Date: Aug. 27, 2024

(87) PCT Pub. No.: WO2023/160999
PCT Pub. Date: Aug. 31, 2023

(65) Prior Publication Data

US 2025/0160898 A1 May 22, 2025

(30) Foreign Application Priority Data

Feb. 28, 2022 (DE) ..................... 10 2022 202 037.5

(51) Int. Cl.
*A61B 17/68* (2006.01)

(52) U.S. Cl.
CPC .................................. *A61B 17/688* (2013.01)

(58) Field of Classification Search
CPC .................................................... A61B 17/688
See application file for complete search history.

(56) References Cited

U.S. PATENT DOCUMENTS 2,340,423 A * 2/1944 O'Shaughnessy, Jr. ..................... F16B 19/1081 29/512
5,707,373 A * 1/1998 Sevrain ................ A61B 17/688 411/338

(Continued)

FOREIGN PATENT DOCUMENTS

DE 102004054122 A1 5/2006
JP 2000157555 A 6/2000

OTHER PUBLICATIONS

Search Report received in International Application No. PCT/EP2023/052850 dated May 19, 2023, with translation, 7 pages.

*Primary Examiner* — Nicholas W Woodall
(74) *Attorney, Agent, or Firm* — Christopher A. Rothe; CM Law

(57) ABSTRACT

An implant for fixing a cranial bone flap in a cranial opening includes a first portion designed to transfer force to the bone flap, a second portion designed to transfer force to a skull bone encircling the cranial opening, and a mechanism connected to the first portion and the second portion. The mechanism is configured such that a transverse spacing, projected onto a transverse axis of the implant, between the first portion and the second portion, is enlargeable, such that the first portion is pressable radially inwardly against the bone flap, and the second portion is pressable radially outwardly against the skull bone. The first portion and/or the second portion are designed for arrangement in an annular gap formed between an outer circumference of the bone flap and an inner circumference of the skull bone. At least two of such implants can make up an implant system.

10 Claims, 19 Drawing Sheets

(56) References Cited

U.S. PATENT DOCUMENTS

| | | | | |
|---|---|---|---|---|
| 6,126,663 | A | 10/2000 | Hair | |
| 6,197,030 | B1 | 3/2001 | Pham | |
| 6,355,044 | B1* | 3/2002 | Hair | A61B 17/688 606/326 |
| 9,095,389 | B2* | 8/2015 | Graham | A61B 17/80 |
| 2002/0095156 | A1 | 7/2002 | Kuras et al. | |
| 2004/0210224 | A1* | 10/2004 | Ahmad | A61B 17/88 606/907 |
| 2007/0173844 | A1* | 7/2007 | Ralph | A61B 17/688 606/916 |
| 2008/0039837 | A1* | 2/2008 | Gambale | A61C 8/0018 606/326 |
| 2010/0168871 | A1* | 7/2010 | Liao | A61F 2/2875 623/23.72 |
| 2013/0053900 | A1* | 2/2013 | Qwarnstrom | A61B 17/688 264/279 |
| 2013/0282011 | A1* | 10/2013 | Brogan | A61B 17/688 606/86 R |
| 2015/0150612 | A1* | 6/2015 | Stephan | A61B 17/8635 606/326 |
| 2024/0122626 | A1* | 4/2024 | Kaiser | A61B 17/688 |

* cited by examiner

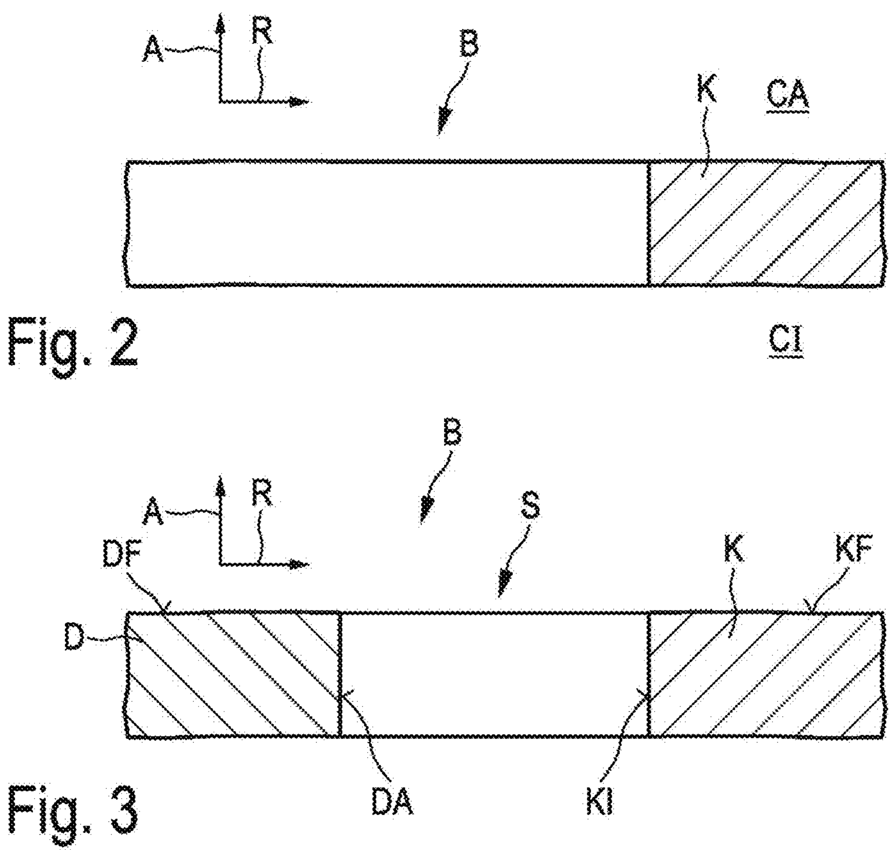
A
R
B
K
CA
Fig. 2
CI
B
A
R
S
DF
K
KF
D
DA
KI
Fig. 3
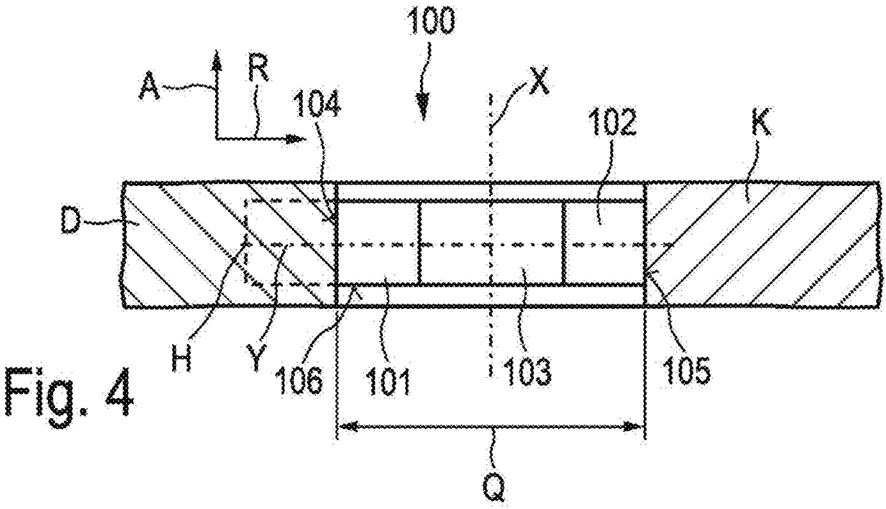
100
A
R
104
X
102
K
D
H
Y
106
101
103
105
Fig. 4
Q

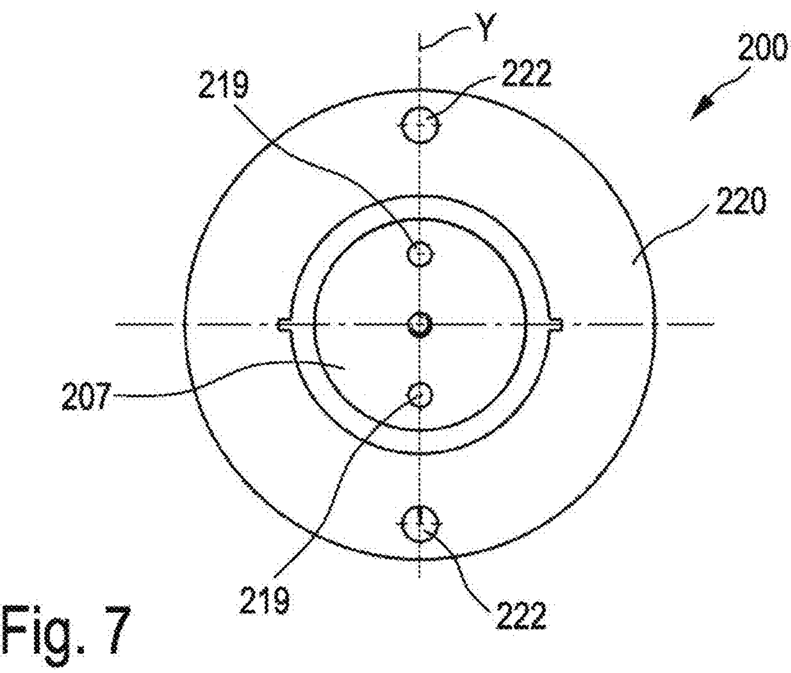
Fig. 7
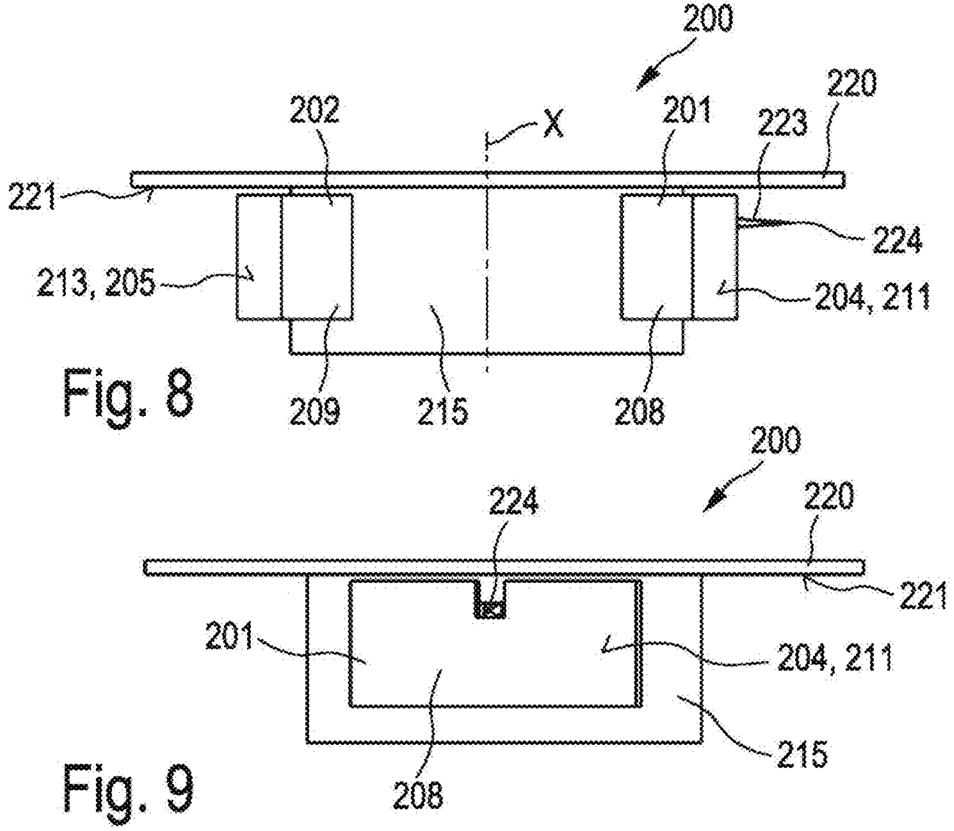
Fig. 8
Fig. 9

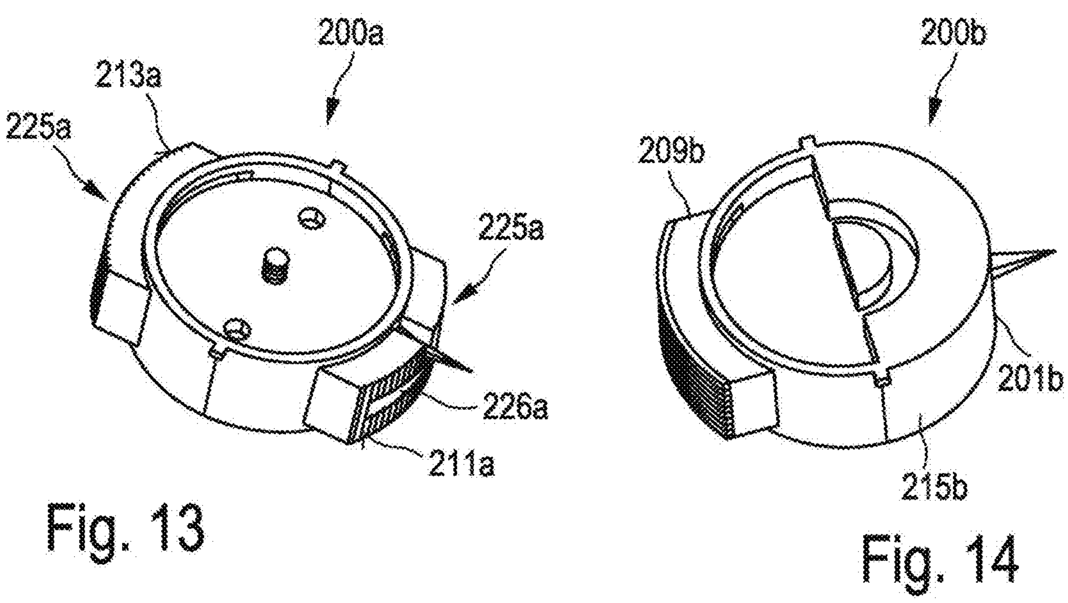
Fig. 13
Fig. 14
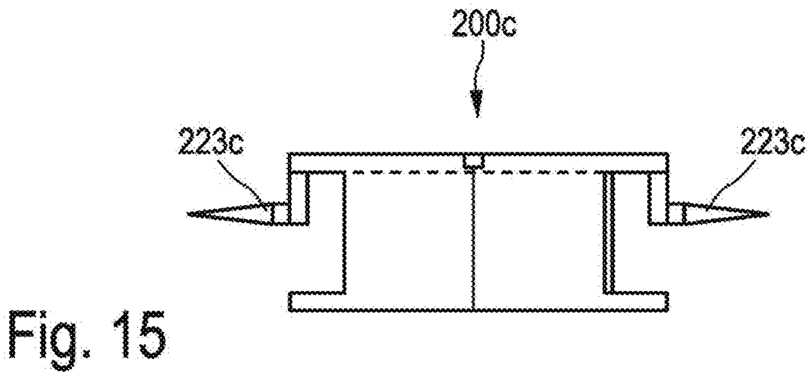
Fig. 15
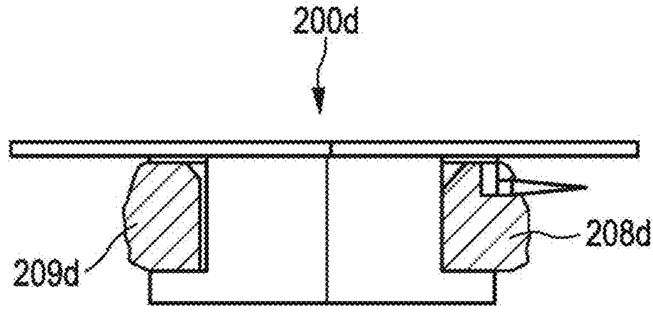
Fig. 16

300
X
G
319
320
303
323
323
307
301
302
312
308, 311
309
310

X
300
319
320
307
323
Y
324
302
313
310

300
319
320
323
323
324
324
307
310
309
302
301
312

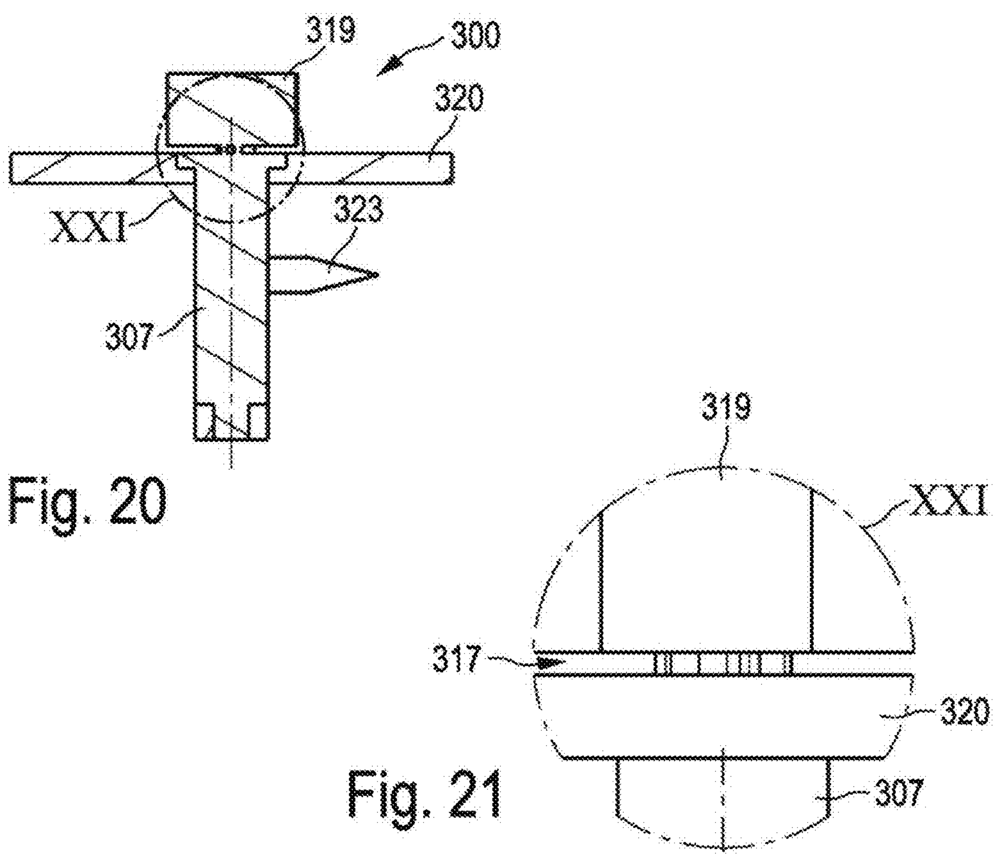
Fig. 20
Fig. 21
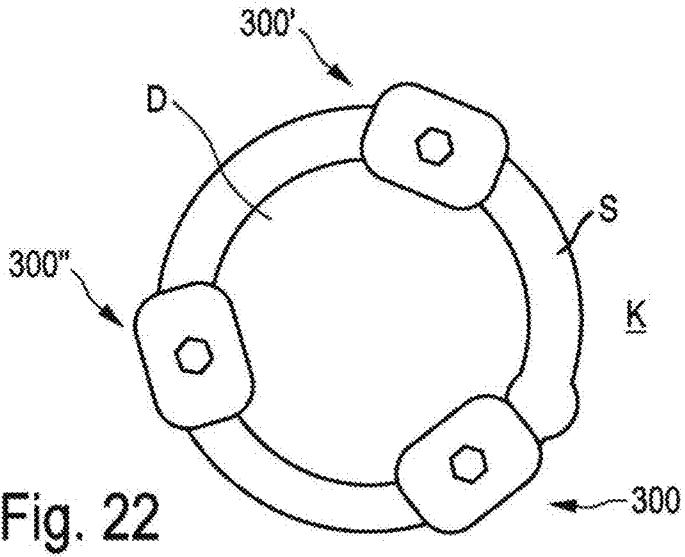
Fig. 22

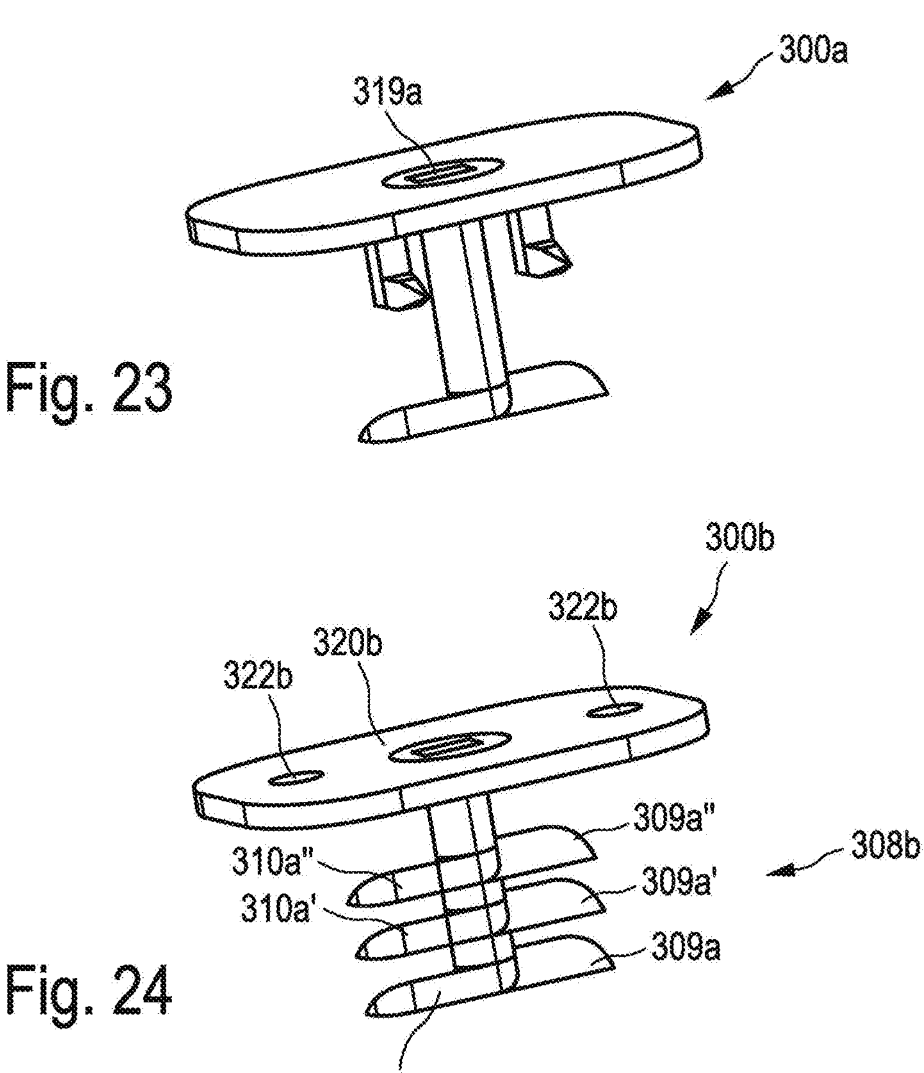
Fig. 23
Fig. 24
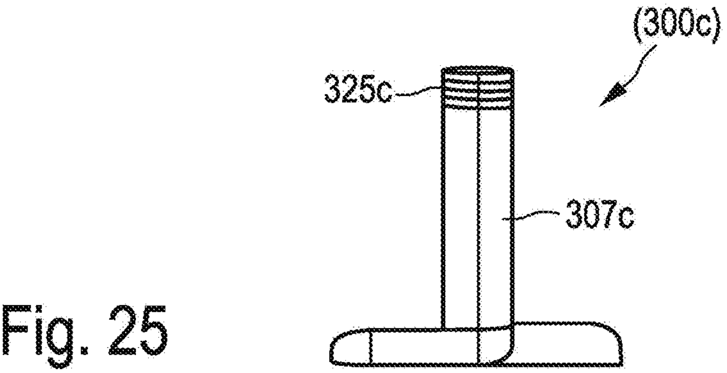
Fig. 25

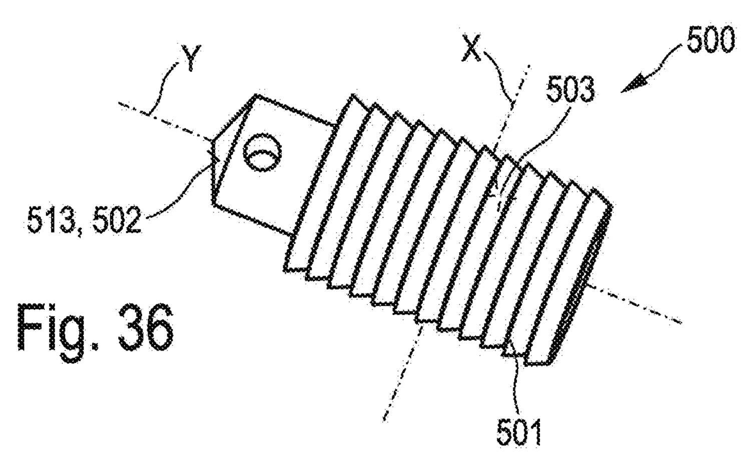
Fig. 36
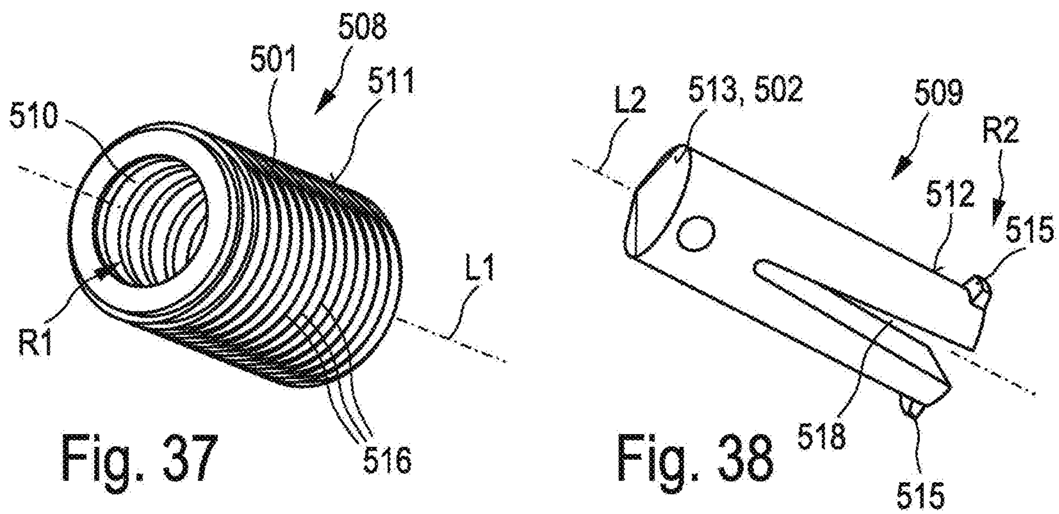
Fig. 37
Fig. 38
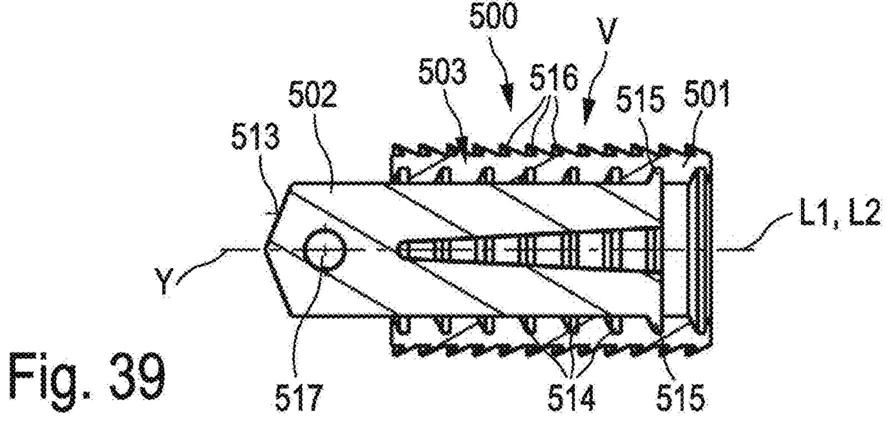
Fig. 39

508a
Va
500a
R1a, R2a
509a

530b
D
511b
500b
509b
H
508b

515c
Vc
500c
508c
509c
514c 509d
508d
500d
511d
R2d
513d
R1d
516d

IMPLANT FOR FIXING A CRANIAL BONE FLAP IN A CRANIAL OPENING

CROSS-REFERENCE TO RELATED APPLICATIONS

This application is the United States national stage entry of International Application No. PCT/EP2023/052850, filed on Feb. 6, 2023, and claims priority to German Application No. 10 2022 202 037.5, filed on Feb. 28, 2022. The contents of International Application No. PCT/EP2023/052850 and German Application No. 10 2022 202 037.5 are incorporated by reference herein in their entireties.

FIELD

The invention relates to an implant for fixing a cranial bone flap in a cranial opening.

BACKGROUND

Neurosurgical procedures on the brain are generally performed through an opening in the bony skull. The production of such a cranial opening is also referred to as craniotomy. In a craniotomy, a part of the skull bone is detached from the bony skull, for example by trepanation. The detached part is also referred to as bone flap or bone fragment. After the procedure is finished, the bone flap is repositioned and fixed in the cranial opening produced beforehand.

To fix the bone flap, implants in the form of what are referred to as clamp systems are known. For example, a clamp system marketed under the trademark CRANIOFIX®2 from Aesculap AG, Tuttlingen, Germany, is known. The known clamp system has an upper disk element, a lower disk element and a rod element which movably connects the two disk elements to one another. The rod element is elongate along a longitudinal axis between the upper end and the lower end, the upper disk element being mounted at the upper end and the lower disk element being mounted at the lower end. To fix the bone flap, firstly the lower disk element is placed in the epidural space, the rod element being aligned approximately parallel to the axial direction of the cranial opening. The bone flap is repositioned in the cranial opening, its inner side being placed onto the lower disk element. Here, the rod element extends from the skull inner side, through the annular gap formed between the bone flap and the surrounding skull bone, to the skull outer side. For final fixing, the upper disk element is moved closer to the lower disk element along the rod element- and thus in the axial direction of the cranial opening. Screwing or latching mechanisms are established for this. In the final fixing state, the two disk elements are pressed both fixedly onto the outer side and fixedly onto the inner side of the bone flap and of the surrounding skull bone in the axial direction of the cranial opening.

Different aspects can be considered to be disadvantageous as regards the known clamp system: The arrangement of the lower disk element in the epidural space can under certain conditions result in irritation of the dura mater and, in the worst case, result in an epidural hematoma. This is because the axial clamping of the disk elements bears the risk of applying unintended pressure to the dura mater, and this can ultimately result in said epidural hematoma. In order to avoid unintended application of compressive force to the dura mater, a special tool for holding the rod element is provided in the case of a clamping system marketed under the trademark CRANIOFIX®2. The additionally required tool can result in impeded handling overall. Moreover, the upper disk element permanently remains on the skull outer side after the fixing has been done. This is disadvantageous in particular in cosmetically critical regions, for example in the case of a frontal craniotomy. Since the upper and the lower disk element must lie on the skull bone and the bone flap as flatly as possible for satisfactory fixing, fixing is often not possible, or not satisfactorily possible, in the case of considerable skull curvatures or thickness gradients. Considerable curvatures can moreover result in the upper disk element protruding from the skull outer side, and this can result in insufficient cosmetic results or scalp irritation.

SUMMARY

An object of the invention is to provide an implant of the type mentioned in the introduction which offers advantages over the prior art. In particular, the intention is to at least partially overcome or mitigate the disadvantages involved in the prior art.

The implant according to the invention for fixing a cranial bone flap in a cranial opening, comprises: a longitudinal axis, which is aligned along an axial direction of the cranial opening, a transverse axis, which is aligned along a radial direction of the cranial opening, a first portion, which is designed to transfer force to the bone flap, a second portion, which is designed to transfer force to a skull bone encircling the cranial opening, wherein the first portion and/or the second portion is designed for arrangement in an annular gap formed between an outer circumference of the bone flap and an inner circumference of the skull bone, and a mechanism, which is operatively connected to the first portion and the second portion and by means of which a transverse spacing, projected onto the transverse axis, between the first portion and the second portion can at least be enlarged, as a result of which the first portion can be pressed radially inwardly against the bone flap and the second portion can be pressed radially outwardly against the skull bone. The solution according to the invention enables radial fixing—with respect to the orientation of the cranial opening. The forces applied for fixing by means of the implant to the bone flap, for the one part, and to the surrounding skull bone, for the other part, therefore act radially. In other words, the applied forces act in the plane of the skull bone or of the bone flap and not, for instance, in their thickness direction. This is in contrast to the solutions known from the prior art, which provide axial fixing. The radial fixing avoids unintended application of compressive force to the dura mater and the associated risks. It is assumed that a radial application of force, i.e. an application of force which acts in the plane, can result in improved regeneration of the bony skull. In the case of the solution according to the invention, the application of force necessary for fixing is effected via a modification, more specifically: an enlargement, of the transverse spacing, projected onto the transverse axis, between the first and the second portion. Since the transverse axis is aligned along, preferably parallel to, the radial direction of the cranial opening, the enlargement of the projected transverse spacing causes said radial contact pressure both on the bone flap and on the skull bone. As a result, the annular gap is enlarged in the region of the implant, and this inevitably results in a reduction in the annular gap on a side of the cranial opening diametrically opposite the implant. On said diametrically opposite side, the bone flap and the encircling skull bone are therefore pressed against one another and ultimately fixed by the action of the implant.

The bone to bone contact that occurs here is conducive to improved regeneration. In particular if use is made of multiple implants that are at a spacing in the circumferential direction of the bone flap, such bone to bone contact is not absolutely necessary. The mechanism operatively connected to the first portion and the second portion is designed at least to enlarge the projected transverse spacing between said portions. The enlargement of the transverse spacing can also be referred to as spreading apart or spreading-apart movement. Different configurations of the invention have different mechanisms for generating the spreading-apart movement. For example, the spreading-apart movement can be brought about by a translational and/or rotational movement, in particular relative movement, of the two portions. To transfer force to the bone flap, the first portion has different forms in different configurations of the invention. In one configuration, the first portion acts, preferably directly, on an outer circumference of the bone flap. In a further configuration, the first portion is inserted into a bore which extends radially in the outer circumference of the bone flap. The same applies, mutatis mutandis, to the second portion. The mechanism is preferably designed for manual actuation by the surgeon. The actuation can be effected purely manually or using a tool suitable for this. The longitudinal axis and the transverse axis of the implant are aligned orthogonally to one another. To fix, and/or in a fixed state of, the cranial bone flap, the longitudinal axis is aligned along, preferably parallel to, the axial direction of the cranial opening. The transverse axis in this case is oriented along, preferably parallel to, the radial direction of the cranial opening. In preferred configurations, the mechanism is additionally designed to reduce the projected transverse spacing. A reduction in the projected transverse spacing enables easy detachment of a fixing performed beforehand. This makes revision procedures easier.

In one configuration of the invention, the mechanism is designed for translational displacement of the first portion and/or of the second portion along the transverse axis. To generate said spreading-apart movement, therefore, at least one of the two portions is displaced in translation along the transverse axis. In one configuration, the mechanism permits a displacement of the first portion along the transverse axis, wherein the second portion is fixed relative to the transverse axis. In a further configuration, the mechanism permits a displacement of the second portion along the transverse axis, wherein the first portion is fixed relative to the transverse axis. In a further configuration, the mechanism permits a displacement of both portions along the transverse axis, wherein in this case the portions are displaced in opposite directions.

In a further configuration of the invention, the mechanism is designed for rotational displacement of the first portion and/or of the second portion about the longitudinal axis. In order to generate the spreading-apart movement, in this configuration at least one of the two portions is displaced in rotation about the longitudinal axis. In one configuration, the mechanism permits a rotational displacement of the first portion, wherein the second portion is fixed relative to the longitudinal axis and/or transverse axis. In a further configuration, the mechanism permits a rotational displacement of the second portion, wherein the first portion is fixed relative to the longitudinal axis and/or transverse axis. In a further configuration of the invention, the mechanism brings about a rotational displacement, preferably in the same direction, of both portions about the longitudinal axis.

In a further configuration of the invention, the first portion has a first contact surface, which is designed to radially bear against the outer circumference of the bone flap. As an alternative or in addition, the second portion has a second contact surface, which is designed to radially bear against the inner circumference of the skull bone. In this configuration of the invention, therefore, the force is transferred via a preferably direct contact pairing between the relevant portion and the respective circumferential surface of the associated bone structure, i.e. the bone flap or the surrounding skull bone. This makes it possible to do without in particular special preparation or processing of the respective bone structure, in particular the introduction of bores or the like. The bone flap usually has an approximately round shape. The same applies, mutatis mutandis, to the shape of the cranial opening. Consequently, a curvature of the outer circumference of the bone flap is usually convex. The curvature of the skull bone encircling the cranial opening is therefore concave. The first contact surface and/or the second contact surface preferably has an accordingly complementary curvature. This makes it possible for the first contact surface to bear as far as possible over its entire surface area against the outer circumference of the bone flap and/or for the second contact surface to bear as far as possible over its entire surface area against the inner circumference of the skull bone.

In a further configuration of the invention, the first portion has a joining surface, which is designed for insertion into a bore which extends radially in the outer circumference of the bone flap. Said bore may be made radially in the bone flap in a separate operating step and serves to at least partially receive the first portion. The first portion is cylindrical, its shape complementing the bore, and preferably has a circular cross section. The joining surface preferably comprises at least one outer lateral surface and/or a face end surface of the first portion. For positioning and/or pre-fixing purposes, the first portion is plugged into the bore in the axial direction of the latter. The form fit and/or force fit established here prevents the first portion from inadvertently sliding off of the outer circumference of the bone flap. It is important to acknowledge that the insertion of the first portion, more specifically: its joining surface, into the bore does not yet establish the fixing on its own. The fixing is effected after the first portion has been inserted into the bore and via the application of said spreading-apart movement, i.e. the enlargement of the projected transverse spacing between the first portion and the second portion.

In a further embodiment of the invention, a supporting portion is present, which is arranged above the first portion and the second portion along the longitudinal axis and has an underside, which is designed for supporting on an outer side of the skull bone and an outer side of the bone flap. The supporting portion serves to make it easier to position the implant during the fixing and prevents inadvertent axial displacement toward the epidural space. The underside of the supporting portion faces toward the outer side of the bony skull and/or is oriented along the longitudinal axis. In different configurations, the supporting portion has different shapings, with a plate shape, a disk shape and/or a ring shape being conceivable in particular. In the supported state, the underside rests on the outer side of the bone flap on one side of the annular gap and on the outer side of the skull bone on the opposite side of the annular gap. The supporting portion is elongate along the transverse axis between the bone flap on one side and the skull bone on the other side.

In a further configuration of the invention, the supporting portion is connected to the rest of the implant by means of a detachable joining connection, in particular a bayonet closure. This configuration allows removal of the supporting portion after the fixing has been completed. To this end, said detachable joining connection between the supporting portion and at least one further component and/or portion of the implant is formed. The detachable joining connection is preferably a bayonet closure. Removing the supporting portion after the fixing has been completed makes it possible to reduce the structural height of the implant with respect to the longitudinal axis. In particular, the supporting portion does not permanently remain on the outer side of the bony skull, which would result in an adverse cosmetic, medical and/or other effect.

In a further configuration of the invention, at least one mandrel portion is present, which is elongate along the transverse axis and at one end has a mandrel tip which projects beyond the first portion and is designed to radially pierce into the outer circumference of the bone flap. The mandrel portion is used for pre-fixing between the bone flap and the implant. For the pre-fixing, the bone flap and the implant are manually plugged together by means of the mandrel portion—while they are still away from the cranial opening. To this end, the mandrel tip is designed to radially pierce into the bone flap. In such a pre-fixed state, the bone flap and the implant can be repositioned in the cranial opening together. Only after this is the actual fixing performed. In order to enable successful piercing into the outer circumference of the bone flap, the mandrel tip projects beyond the first portion along the transverse axis. In different configurations, there is a different number of mandrel portions. Multiple mandrel portions are advantageous in particular when the bone flap to be fixed is formed of multiple loose bone fragments. These loose bone fragments can be pre-fixed to the implant together by means of said multiple mandrel portions.

In a further configuration of the invention, the mechanism has at least one clamping element and a cone element, wherein the clamping element is movably mounted along the transverse axis and has an inner cone surface and an end face forming the first portion or the second portion, wherein the cone element is movably mounted along the longitudinal axis and has an outer cone surface interacting with the inner cone surface, and wherein the clamping element can be displaced by means of a movement of the cone element along the transverse axis. The clamping element serves to transfer force to the bone flap or the encircling skull bone, depending on whether the end face forms the first or the second portion. The displacement of the clamping element along the transverse axis is caused by a longitudinal movement of the cone element. The inner cone surface and the outer cone surface are inclined with respect to the longitudinal and/or transverse axis and rest slidingly on one another. As a result, a longitudinal displacement of the cone element causes a transverse displacement of the clamping element. The cone element is preferably designed for direct or indirect manual actuation. Consequently, an application of force or torque required to displace the cone element along the longitudinal axis can be applied directly or indirectly to the cone element manually or using a tool suitable for this.

In a further configuration of the invention, the mechanism has a further clamping element, which can be oppositely displaced by means of the movement of the cone element along the transverse axis. As regards the fundamental function and configuration of the further clamping element, what was said in relation to the clamping element applies, mutatis mutandis. If the end face of the clamping element forms the first portion, an end face of the further clamping element forms the second portion, or vice versa. The clamping element and the further clamping element are preferably offset from one another by 180° in the circumferential direction of the implant.

In a further configuration of the invention, the cone element has a thread, which is screwed to a complementary mating thread for threaded movement along the longitudinal axis. To transfer force and movement to the clamping element, therefore, the cone element can be moved in screw-like fashion along the longitudinal axis. With preference, the thread is an internal thread and the complementary mating thread is an external thread. The complementary mating thread is stationary with respect to the longitudinal axis. Owing to the mounting for threaded movement, an application of torque directed about the longitudinal axis brings about a rotational displacement about and a translational displacement along the longitudinal axis. In other words, in this configuration the cone element can be unscrewed in the direction of the skull inner side, and/or screwed on in the direction of the skull outer side, along the longitudinal axis. In an alternative configuration, instead of mounting of the cone element for threaded movement, mounting of the cone element for latching movement is provided.

In a further configuration of the invention, the mechanism has an axis of rotation, which is oriented along the longitudinal axis, and an eccentric element, which is movably mounted about the axis of rotation and has a contour which is eccentric with respect to the axis of rotation, wherein different portions of the contour form the first portion and the second portion, and wherein a rotation of the eccentric element causes the contour to be clamped between the outer circumference of the bone flap and the inner circumference of the skull bone. The first portion and the second portion are preferably arranged diametrically opposite on the eccentric element with respect to the axis of rotation. In different configurations, the eccentric contour has different shapes and, for example in the broadest sense, is unround, oval, elongate or the like. The axis of rotation is preferably oriented parallel to the longitudinal axis. Rotating the eccentric element about the axis of rotation causes the first and the second portion to come to bear against the respective bone structure. Further rotation of the eccentric element causes-owing to the eccentric contour—the first portion to be radially pressed against the bone flap on one side and the second portion to radially press against the encircling skull bone on the other side. As a result, the eccentric element is clamped within the annular gap, the radial spacing between the outer circumference of the bone flap and the inner circumference of the skull bone is enlarged in the region of the eccentric element, and therefore a region of the annular gap diametrically opposite the implant is reduced and lastly completely closed to establish bone to bone contact between the bone flap and the encircling skull bone.

In a further configuration of the invention, a shaft element is present, at one end of which the eccentric element is arranged and at the other end of which a tool fitting element is arranged, wherein the tool fitting element is designed to apply a torque directed about the axis of rotation. The shaft is elongate along, preferably parallel to, the longitudinal axis. The tool fitting is arranged at a first end and the eccentric element is arranged at a second end of the shaft element. The eccentric element and the tool fitting element are connected fixedly to each other by means of the shaft element, with the result that a rotation of the tool fitting element brings about a corresponding rotation of the shaft element and of the eccentric element. In different configurations, the tool fitting element has a different form and is designed for the fitting of a tool. For example, the tool fitting element may have a hexagonal socket, a hexagonal head, a cross-head slot or a slot.

In a further configuration of the invention, the tool fitting element forms an upper face end, with respect to the longitudinal axis, of the implant and is connected to the shaft element via a predetermined breaking portion. The predetermined breaking portion breaks under the action of defined mechanical loading. This makes it possible to shear and/or break the tool fitting element off of the shaft element in a defined way after the fixing has been completed. Since in this configuration the tool fitting element forms the upper face end of the implant, this reduces the structural height of the implant with respect to the longitudinal axis. In particular, the tool fitting element does not permanently remain on the outer side of the bony skull after the fixing has been completed, which would result in adverse cosmetic, medical and/or other effects. The predetermined breaking portion is arranged between the tool fitting element and the shaft element with respect to the longitudinal axis. In comparison with the shaft element, the predetermined breaking portion has a smaller load-bearing cross section. As a result, one and the same instance of mechanical loading therefore leads to locally higher mechanical stress in the region of the predetermined breaking portion and ultimately to local mechanical failure.

In a further configuration of the invention, the eccentric element has at least a first blade portion, which forms the first portion, and a second blade portion, which is offset about the axis of rotation and forms the second portion, wherein the blade portions each project radially from the axis of rotation with a longitudinal extent and have oppositely oriented cutting edges. In this configuration of the invention, the eccentric element has an eccentric, in the broadest sense elongate contour. This contour is partially formed by the first blade portion and the second blade portion. When the eccentric element is clamped, the blade portions, more specifically: their cutting edges, each penetrate the associated bone structure. Specifically, the cutting edge of the first blade portion enters the outer circumference of the bone flap. The cutting edge of the second blade portion enters the inner circumference of the skull bone. Particularly reliable fixing is achieved as a result. In different configurations, there are different numbers of blade portions. For example, one configuration provides that multiple blade portions are arranged in pairs in planes arranged one above another with respect to the longitudinal axis.

In a further configuration of the invention, the mechanism has a pressure element and a spring element, wherein the pressure element is elongate and movably mounted along the transverse axis between a first face end, which forms the first portion or the second portion, and a second face end, wherein the spring element is supported at least indirectly on the second face end, and wherein the pressure element is biased with a spring force along the transverse axis by means of the spring element. Depending on the orientation of the pressure element and the arrangement of the spring element, the first face end of the pressure element forms either the first portion or the second portion. Consequently, the pressure element can be pressed by means of the spring element either against the bone flap or against the encircling skull bone. The spring force of the spring element acts along the transverse axis. For fixing purposes, the pressure element can be displaced, for example manually, counter to the spring force along the transverse axis and as a result the projected transverse spacing between the first portion and the second portion can be reduced. After pre-positioning has been completed, the manual pressure on the pressure element can be released, as a result of which the spring presses the pressure element against the corresponding bone structure. In an alternative configuration, the pressure element is releasably locked counter to the application of spring force in a rear end position with respect to the transverse axis. After the locking is released, the spring force pushes the pressure element along the transverse axis against the corresponding bone structure.

In a further configuration of the invention, a locking element is present, which can be displaced relative to the pressure element between a locking position, in which the locking element fixes the pressure element with respect to the transverse axis counter to the spring force of the spring element, and a release position, in which the pressure element is free to move along the transverse axis. The displacement of the locking element between the locking and the release position is preferably effected manually. In the locking position, a portion of the locking element is detachably form-fittingly and/or force-fittingly connected to a portion of the pressure element. A displacement in the direction of the release position detaches said connection between the locking element and the pressure element. After the connection has been detached, the pressure element is free to move along the transverse axis, with the result that the spring force leads to the first face end being pressed against the associated bone structure (bone flap or skull bone) depending on the configuration.

In a further configuration of the invention, the mechanism has a first cylinder element and a second cylinder element, the longitudinal axes of which are coaxial and are aligned parallel to the transverse axis, wherein the first cylinder element has a profiled first cylinder lateral surface and a first surface forming the first portion, wherein the second cylinder element has a second cylinder lateral surface with a complementary profile and a second surface which forms the second portion, wherein the first cylinder lateral surface and the second cylinder lateral surface can be connected to one another to form a connection, which is form fitting and/or force fitting along the transverse axis, in different axial relative positions of the cylinder elements. Different axial relative positions bring about a different transverse spacing between the first surface and the second surface. In other words, the first cylinder element and the second cylinder element are joined to each other along the transverse axis. In one configuration, the first cylinder element is inserted in the second cylinder element, wherein in this case the profiled first cylinder lateral surface is an outer lateral surface and the profiled second cylinder lateral surface is an inner lateral surface. In a further configuration, the second cylinder element is inserted in the first cylinder element, wherein in this case the profiled first cylinder lateral surface is an inner lateral surface and the profiled second cylinder lateral surface is an outer lateral surface. In both cases, one of the two cylinder elements acts as a type of bushing and the remaining cylinder element acts as a type of bolt, pin or the like. The profilings present on the cylinder lateral surfaces can each be in the form of a latching geometry or threaded geometry. Accordingly, in one configuration the connection is a latching connection and in a further configuration it is a screwed connection. In the latter configuration, the two cylinder elements are unscrewed from one another to enlarge the transverse spacing, but of course are not completely detached from one another. In the configuration with a latching connection, it is latched over on one side to enlarge the transverse spacing.

In a further configuration of the invention, the second surface is a face end surface of the second cylinder element and is designed to radially bear against the inner circumference of the skull bone, and the first surface is on the outer lateral surface of the first cylinder element and is designed for insertion into a bore which extends radially in the outer circumference of the bone flap. In this configuration, the implant is firstly joined to the bone flap for pre-fixing purposes. To this end, the outer lateral surface of the first cylinder element is plugged into the radial bore prepared in the bone flap. In this case, the first cylinder element can be inserted either loosely or force-fittingly, form-fittingly and/or integrally into the radial bore. After the pre-fixing has been completed, the bone flap together with the implant attached to it can be positioned in the cranial opening. For the actual fixing, the two cylinder elements are displaced relative to each other along the transverse axis. This is done for example via the latching or screwed connection described above. The relative displacement brings about an enlargement of the transverse spacing, with the result that the annular gap is enlarged in the region of the implant, reduced on a diametrically opposite side, and ultimately completely closed to form bone to bone contact between the bone flap and the encircling skull bone.

In a further configuration of the invention, the first cylinder lateral surface is an outer lateral surface and the second cylinder lateral surface is an inner lateral surface. In this configuration, therefore, the first cylinder element is inserted in the second cylinder element. To modify the transverse spacing between the opposite face end surfaces of the cylinder elements, i.e. the first and the second portion, the first cylinder element can be displaced axially further into the second cylinder element or displaced axially out of it.

In a further configuration of the invention, the first cylinder lateral surface and the second cylinder lateral surface each have a profiling in the form of a latching geometry and are latched to one another along the transverse axis such that one can be latched over the other on one side. The latching geometry of the first cylinder lateral surface complements the latching geometry of the second cylinder lateral surface, and vice versa. One can be latched over the other on one side means that the latching connection formed between the latching geometries always acts form-fittingly in one direction along the transverse axis, with the result that a transverse movement in this direction is completely prevented. The latching connection can be latched over in the opposite direction, with the result that the two cylinder elements can be connected to one another in different axial relative positions.

In a further configuration of the invention, the first cylinder lateral surface and the second cylinder lateral surface each have a profiling in the form of a threaded geometry and are screwed to one another for threaded movement along the transverse axis.

The invention also relates to an implant system having at least two implants according to the description above.

BRIEF DESCRIPTION OF THE DRAWINGS

Further advantages and features of the invention will emerge from the following description of preferred exemplary embodiments of the invention that are illustrated by the drawings.

FIG. 2 shows a schematically simplified cross-sectional illustration of the skull according to FIG. 1 in the region of the cranial opening, the bone flap being hidden in the drawing;

FIG. 3 shows the region illustrated by means of FIG. 2 with the bone flap superposed;

FIG. 4 shows the region shown by means of FIGS. 2 and 3, with an embodiment of an implant according to the invention for fixing the bone flap in the cranial opening;

FIG. 7 shows a schematic view of the implant according to FIGS. 5 and 6;

FIG. 8 shows a schematic side view of the implant according to FIGS. 5 to 7;

FIG. 9 shows a further side view, rotated by 90°, of the implant according to FIGS. 5 to 8;

FIG. 13 shows a schematic perspective illustration of a first variant of the implant according to FIGS. 5 to 9;

FIG. 14 shows a schematic perspective illustration of a second variant of the implant according to FIGS. 5 to 9;

FIG. 15 shows a schematic sectional view of a third variant of the implant according to FIGS. 5 to 9;

FIG. 16 shows a schematic side view of a fourth variant of the implant according to FIGS. 5 to 9;

FIG. 20 shows a schematic illustration, in longitudinal section, of the implant according to FIGS. 17 to 19;

FIG. 21 shows an enlarged detail illustration of a region XXI of the implant according to FIGS. 17 to 20;

FIG. 22 shows an intraoperative situation using the implant according to FIGS. 17 to 21;

FIG. 23 shows a schematic perspective illustration of a first variant of the implant according to FIGS. 17 to 21;

FIG. 24 shows a schematic perspective illustration of a second variant of the implant according to FIGS. 17 to 21;

FIG. 25 shows a schematic perspective illustration of a third variant of the implant according to FIGS. 17 to 21 with individual components and/or portions of the implant being hidden in the drawing;

FIG. 36 shows a schematic perspective illustration of a further embodiment of an implant according to the invention with a first cylinder element and a second cylinder element;

FIG. 37 shows a schematic perspective illustration of the first cylinder element of the implant according to FIG. 36;

FIG. 38 shows a schematic perspective illustration of the second cylinder element of the implant according to FIG. 36;

FIG. 39 shows the implant according to FIG. 36 in a schematic illustration in longitudinal section;

DETAILED DESCRIPTION

Figure 1:
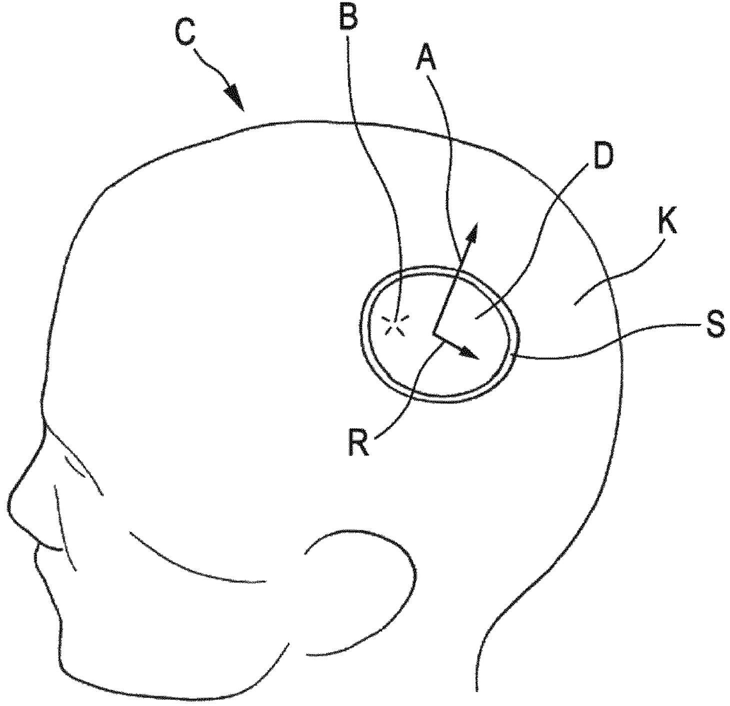
FIG. 1 shows a schematically highly simplified perspective illustration of a patient's head, the patient's bony skull having a cranial opening closed with a bone flap.
Figure 5:
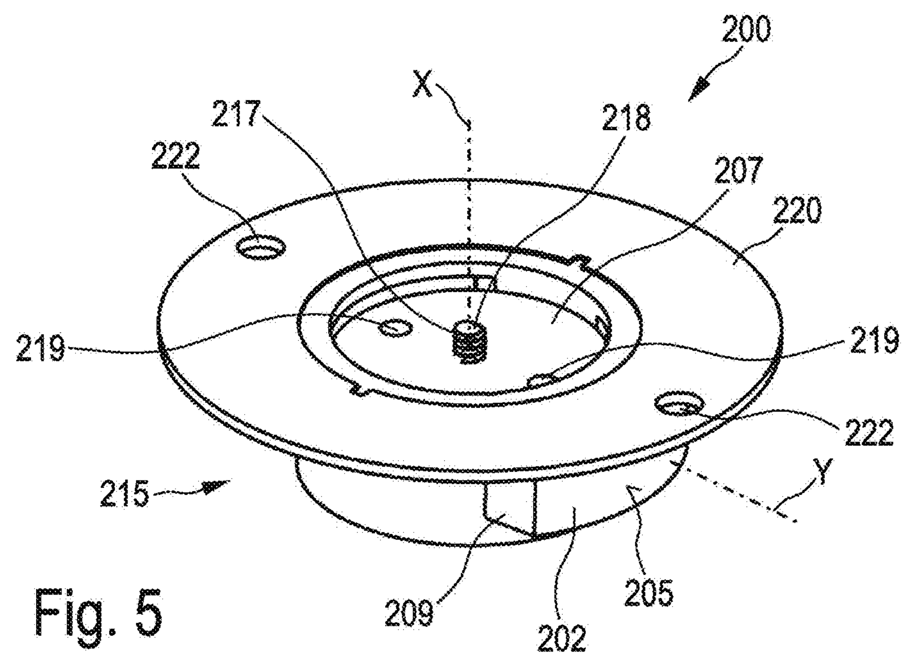
FIG. 5 shows a schematic perspective illustration of a further embodiment of an implant according to the invention.
Figure 6:
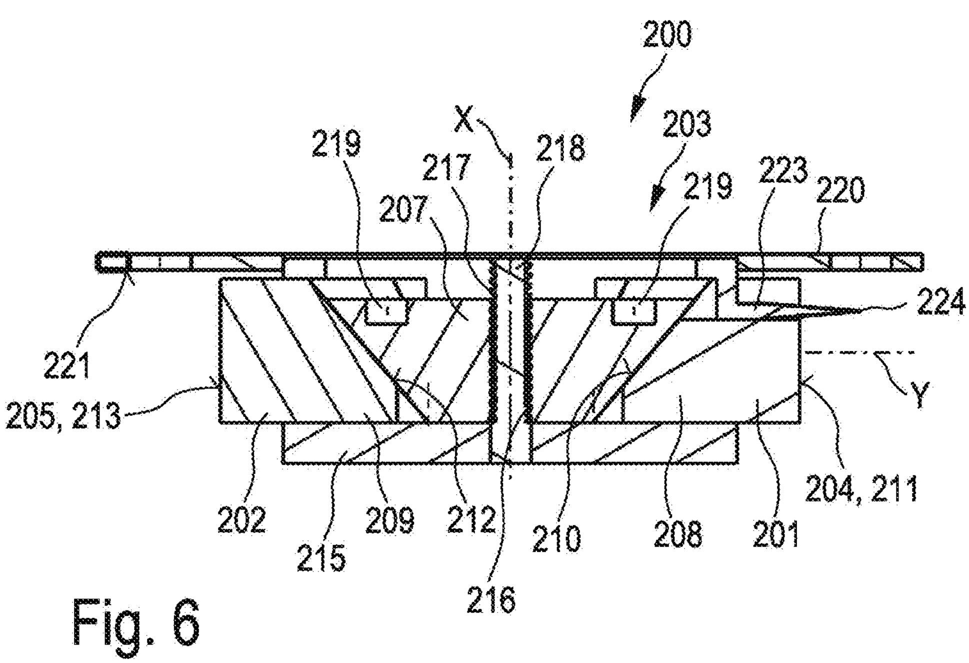
FIG. 6 shows a schematic illustration, in longitudinal section, of the implant according to FIG. 5.

According to FIG. 1, a patient's head has a cranial opening B, which extends from a bone outer side CA, through the patient's bony skull C to a skull inner side CI (FIG. 2). The cranial opening B extends along its axial direction A through the bony skull C. Along its radial direction R, the cranial opening B is encircled by skull bone K.

The cranial opening can in principle be caused by an accident or some other unintended action. In the present case, the cranial opening B is the result of a craniotomy and serves as surgically produced access for a neurosurgical procedure on the patient's brain.

During such a craniotomy, the bony skull C is opened by mechanically detaching a bone flap D. This can be effected, for example, by means of trepanation. Here, the bone flap D is detached from the bony skull C to form an annular gap S. The annular gap S is also referred to as craniotomy gap. The bone flap D may also be referred to as bone part, bone fragment or bone segment.

After the bone flap D has been detached, it can be temporarily removed from the rest of the bony skull to form the actual cranial opening B. After the procedure on the brain has been completed, the bone flap D is repositioned and fixed in the opening B.

According to FIG. 4, an implant 100 for fixing the cranial bone flap D in the cranial opening B is provided. The implant 100 has a longitudinal axis X, a transverse axis Y, a first portion 101, a second portion 102 and a mechanism 103.

The longitudinal axis X is aligned along the axial direction A of the cranial opening B. The transverse axis Y, which is oriented orthogonally to the longitudinal axis X, is aligned along the radial direction R of the cranial opening B. Said alignments of the longitudinal axis X and the transverse axis Y relate to the configuration shown by means of FIG. 4, in which configuration the bone flap D is fixed by means of the implant 100.

The first portion 101 is designed to transfer force to the bone flap D. Accordingly, the first portion 101 faces toward the bone flap D.

The second portion 102 is designed to transfer force to the skull bone K encircling the cranial opening B. Accordingly, the second portion faces toward the skull bone K.

The mechanism 103 is operatively connected to the first portion 101 and to the second portion 102 and is designed to modify a transverse spacing Q, projected onto the transverse axis Y, between the first portion 101 and the second portion 102. As a result of said enlargement of the transverse spacing Q, the first portion 101 can be pressed radially R inward against the bone flap D and the second portion 102 can be pressed radially R outward against the skull bone K. The transfer of force between the first portion 101 and the bone flap D, on one side, and the second portion 102 and the skull bone K, on the other side, is performed along the radial direction R, and therefore it can also be referred to as a radial fixing.

To fix the bone flap D, the implant 100 is introduced into the annular gap S along the axial direction A. The first portion 101 is oriented radially R inward, i.e. in the direction toward the bone flap D. The second portion 102 is oriented radially R outward, i.e. in the direction toward the skull bone K. After this, the mechanism 103 is actuated to enlarge the transverse spacing Q. This actuation can be effected directly or indirectly using a tool or purely manually. The actuation of the mechanism brings about said enlargement of the transverse spacing Q. Owing to the enlargement of the transverse spacing Q, the first portion 101 acts radially R inward on the bone flap D and the second portion 102 acts radially R oppositely outward on the bone flap K. As a result, the annular gap S is enlarged locally, i.e. in the region of the implant 100. The local enlargement of the annular gap S is inevitably involved with a local reduction of the annular gap S on a side of the bone flap D diametrically opposite the implant 100 in the radial direction R. In this region, the bone flap D is pushed against the skull bone K by the action of the implant 100 in the radial direction R. This establishes bone to bone contact and the bone flap D is fixed in the opening B via being clamped in the radial direction R.

In principle, it is sufficient if a single implant is used for the fixing. It is self-evident, however, that more than one implant can also be used. If multiple implants are used, they are arranged in the annular gap S at a spacing from one another in the circumferential direction. The multiple implants are then radially clamped between the bone flap D and the encircling skull bone K via an enlargement of their projected transverse spacing Q. Fixing by means of multiple implants will be described in more detail below.

In different embodiments, the mechanism takes different forms. A very wide variety of structures for enlarging the transverse spacing Q, i.e. for generating the spreading movement or spreading-apart movement between the two portions, are conceivable. For example, the mechanism may be based on a screw or thread principle, a scissor joint mechanism, a wedge, cone and/or clamping mechanism, a latching mechanism, an eccentric mechanism or the like. In this case, the enlargement of the transverse spacing Q brought about by the mechanism can be based on a translational and/or rotational displacement of the first portion and/or of the second portion. For example, the first portion may be radially inwardly displaceable along the transverse axis Y, the second portion being stationary with respect to the transverse axis Y, or vice versa. The same applies, mutatis mutandis, to a rotational displacement about the longitudinal axis X.

The transfer of force between the two portions and the respective associated bone structure, i.e. the bone flap D on one side and the skull bone K on the other side, can be effected directly or indirectly. Directly means that direct contact is established between the respective portion and the corresponding bone structure. Indirectly means that further components or elements of the implant can be arranged between the respective portion and the respective associated bone structure D, K.

Here, the transfer of force to the bone flap D can be effected for the one part to its outer circumference DA. As an alternative or in addition, the force can be transferred via a bore H made in the bone flap D, as indicated in dashed line in FIG. 4. The same applies, mutatis mutandis, for the transfer of force to the skull bone K. This means that force can be transferred for the one part to the inner circumference KI of the skull bone K. It is also fundamentally conceivable for a bore or the like to be made in the skull bone K in the radial direction R in order to transfer force.

In the case of the implant 100 according to FIG. 4, force is transferred directly to the respective circumference of the bone structure. Consequently, the first portion 101 has a first contact surface 104. This first contact surface is designed to (directly) radially bear against the outer circumference DA of the bone flap D. The second portion 102 has a second contact surface 105. This second contact surface is designed to (directly) radially bear against the inner circumference KI of the skull bone K. An unspecified normal direction of the first contact surface 104 points parallel to the transverse axis Y and radially inward in the present case. An unspecified normal direction of the second contact surface 105 points parallel to the transverse axis Y and radially outward in the present case. Consequently, the contact surfaces 104, 105 are oriented oppositely to one another.

Also in relation to FIG. 4, the first portion 101 has a joining surface 106. The joining surface 106 in particular has an effect when the bone flap D is provided with a bore H. In this case, the portion 101, more specifically: its joining surface 106, can be inserted into the bore H. In this case, force is transferred not to the outer circumference DA, but instead via the unspecified walls of the bore H.

In the case of the implant 100 according to FIG. 4, the first portion 101, the second portion 102 and the mechanism 103 are arranged completely within the annular gap S. The overall implant 100 is arranged between the outer circumference DA of the bone flap D and the inner circumference KI of the skull bone K with respect to the radial direction R and thus also the transverse direction Y. The overall implant 100 is arranged between the skull outer side CA and the skull inner side CI with respect to the axial direction A and thus also the longitudinal axis X. Consequently, the implant 100 does not project upward or downward out of the annular gap S along the longitudinal axis X.

FIGS. 5 to 16 show a further embodiment of an implant 200 according to the invention, with FIGS. 13 to 16 relating to variants of this embodiment.

With regard to FIGS. 5 to 9, the implant 200 has a longitudinal axis X, a transverse axis Y, a first portion 201, a second portion 202 and a mechanism 203. The mechanism 203 has a cone segment 207, a first clamping element 208 and a second clamping element 209.

The two clamping elements 208, 209 are each movably mounted along the transverse axis Y.

The first clamping element 208 has a first inner cone surface 210 and a first end face 211. The first inner cone surface 210 is on the inside with respect to the longitudinal axis X, and the first end face 211 is correspondingly on the outside. The first end face 211 is designed to radially bear against the outer circumference DA of the bone flap D and in this respect acts as first contact surface 204. The first clamping element 208 and/or its first end face 211 therefore forms the first portion 201 of the implant 200.

The second clamping element 209 has a second inner cone surface 212 and a second end face 213. The second end face 213 is on the outside with respect to the longitudinal axis X, and the second inner cone surface 212 is on the inside. The second end face 213 is designed to radially bear against the inner circumference KI of the skull bone K and therefore serves as second contact surface 205. The second clamping element 209 and/or its second end face 213 therefore forms the second portion 202 of the implant 200.

The cone element 207 is movably mounted along the longitudinal axis X and has an outer cone surface 214 which slidingly interacts with the two inner cone surfaces 210, 212. The cone element 207 can be displaced between an upper end position, not shown in the figures, and a lower end position (FIG. 6) with respect to the longitudinal axis X. In the upper end position, the two clamping elements 208, 209 are moved toward one another along the transverse axis Y and inward with respect to the longitudinal axis. In the upper end position, therefore, there is a first transverse spacing, not illustrated in more detail, between the first contact surface 204 and the second contact surface 205. A longitudinal displacement of the clamping element 207 from the upper end position in the direction toward the lower end position (FIG. 6) has the effect that the clamping elements 208, 209 are displaced outward along the transverse axis Y with enlargement of the transverse spacing Q. In the process, the longitudinal movement of the cone element 207 is converted into the respective transverse movement of the clamping elements 208, 209 via the interaction of the outer cone surface 214 with the two inner cone surfaces 210, 212. The transmission ratio can be modified in structural terms by adapting the respective inclination, or the cone angle, of the cone surfaces 210, 212, 214.

The implant 200 in the present case has a housing 215 for receiving and/or movably mounting the two clamping elements 208, 209. The housing 215 has a hollow-cylindrical shape with a circular cross section and is provided on opposite sides in the transverse direction Y with unspecified receiving openings, in which the clamping elements 208, 209 are introduced. The receiving openings can also be referred to as pockets.

In the embodiment shown, the cone element 207 is mounted for threaded movement along the longitudinal axis X. To this end, the cone element 207 has a thread 216, which is screwed to a complementary and stationary mating thread 217. In the present case, the thread 216 is an internal thread. The mating thread 217 is accordingly an external thread. In the embodiment shown, the mating thread 217 is formed on a threaded rod 218 with a longitudinal extent parallel to, more specifically: coaxial with, the longitudinal axis X. The threaded rod 218 is secured to the housing 215 at its lower face end with respect to the longitudinal axis X.

In the embodiment shown, the cone element 207 is designed for force and/or torque to be applied to it by means of a tool suitable for this and has corresponding tool fittings 219. The tool fittings 219 are set back from an unspecified top side of the cone element 207 along the longitudinal axis X and in the present case have a circular-cylindrical cross-sectional shape. The tool fittings 219 are offset from one another by 180° in the circumferential direction.

To spread apart the two clamping elements 208, 209—i.e. to enlarge the (projected) transverse spacing-said tool is detachably connected to the tool fittings 219 and a torque directed about the longitudinal axis X is applied. Under the action of the torque, the cone element 207 can be screwed downward along the threaded rod 218, as a result of which the clamping elements 208, 209 are moved out of the housing 215 and spread in this respect.

In the embodiment shown, the implant 200 also has a supporting portion 220, which is arranged above the two clamping elements 208, 209 and the cone element 207 along the longitudinal axis X. In this respect, the supporting portion 220 is arranged above the first portion 201 and the second portion 202. The supporting portion 220 has an underside 221, which is designed for supporting the implant 200 against an outer side KF of the skull bone K on one side and an outer side DF of the bone flap D on the other side (see FIG. 2). The underside 221 is oriented orthogonally to the end faces 211, 213. The supporting portion 220 makes it easier to position the implant 200 within the annular gap S. Said support avoids excessively deep penetration into the annular gap S and associated risks, for example pressure-related irritation of the dura mater, which in the worst case can be associated with an epidural hematoma.

In the embodiment shown, the supporting portion 220 is connected to the rest of the implant 200 by means of a detachable joining connection, more specifically: a bayonet closure. In the present case, the bayonet closure is formed between an unspecified inner circumference of the supporting portion 220 and a geometry of the top side of the housing 215. Instead of the bayonet closure, a routine screwed connection or the like can also be provided, for example. As an alternative, a plug-mounted or latching connection is conceivable. The detachable joining connection makes it possible to detach and remove the supporting portion 220 from the housing 215 after the fixing has been completed. After the supporting portion 220 has been removed, the (rest of the) implant 200 is arranged completely within the annular gap S with respect to the longitudinal direction X. This has cosmetic and medical advantages.

In the embodiment shown, the supporting portion 220 is in the form of a circular disk and has two tool fittings 222 which are offset from one another by 180° in the circumferential direction. The tool fittings 222 serve for fitting of a tool for detaching and/or connecting said bayonet closure. The tool fittings 222 may alternatively or additionally be used as boreholes for pre-fixing the implant 200 to the bone flap D.

In the present case, the implant 200 also has a mandrel portion 223. The mandrel portion 223 is elongate along the transverse axis Y and has a mandrel tip 224, which at one end protrudes beyond the first portion 201, i.e. in the present case the first clamping element 208. This mandrel tip is designed to radially pierce the outer circumference DA of the bone flap D. The mandrel portion 223 is secured at its end remote from the mandrel tip 224 to the housing 215 in a way which is not shown in more detail. The mandrel portion 223 serves to pre-fix the implant 200 to the bone flap D. To this end, the mandrel tip 224 radially pierces the bone flap D. This takes place preferably even before the bone flap D is repositioned inside the opening B.

Figure 10:
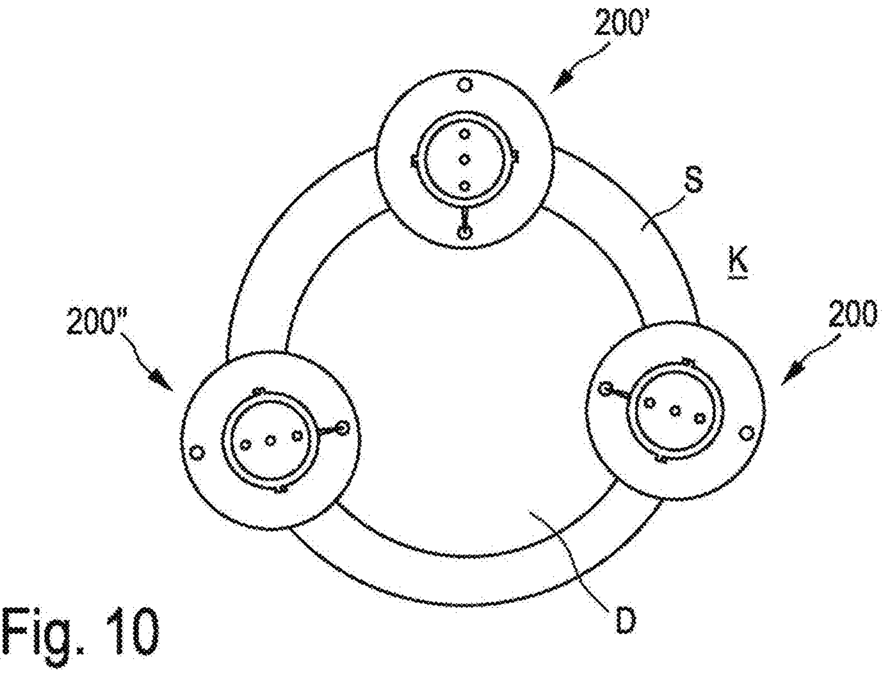
FIG. 10 shows a schematically highly simplified illustration of a first intraoperative situation using the implant according to FIGS. 5 to 9.
Figure 11:
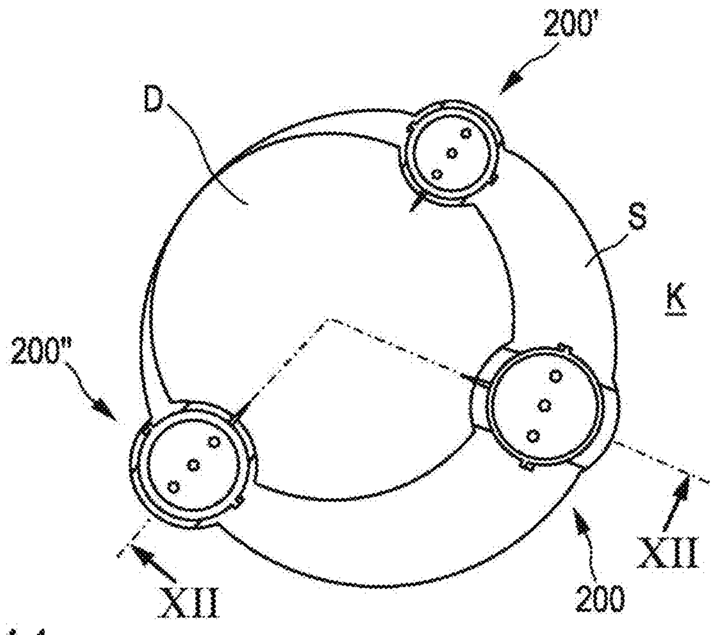
FIG. 11 shows a second intraoperative situation using the implant according to FIGS. 1 to 9.
Figure 12:
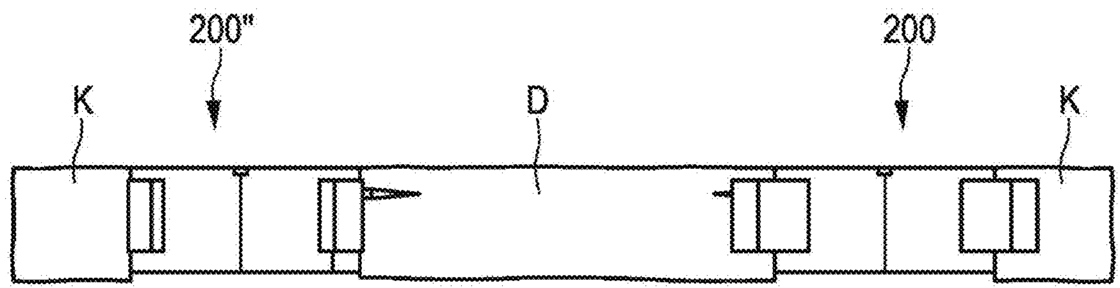
FIG. 12 shows the second intraoperative situation according to FIG. 11 in a schematic sectional view along the section XII-XII.

FIGS. 10 to 12 show a first intraoperative situation (FIG. 10) and a second intraoperative situation (FIGS. 11 and 12) using the implant 200. The first intraoperative situation shows a pre-fixed state of the bone flap D and the second intraoperative situation shows an ultimately fixed state. The situational example shown intends the use of multiple structurally identical implants, specifically the implant 200, a second implant 200' and a third implant 200". The implants 200, 200', 200" form an implant system. In the present case, the implants 200, 200', 200" are arranged within the annular gap S so as to be offset approximately by 120° in the circumferential direction of the bone flap D. For pre-fixing purposes, the respective mandrel portion of the implants 200, 200', 200" is plugged in the outer circumference DA of the bone flap D in the way already described. After the implants 200, 200', 200" have been plugged into or plug-mounted with the bone flap D, the arrangement pre-fixed in this respect is (re)positioned together in the cranial opening B. After this, the situation shown in FIG. 10 is produced.

For the actual fixing, in the example shown the first implant 200 is expanded. That is to say, its clamping elements 208, 209 are spread apart in the radial direction R of the opening B via the actuation of the cone element 207 already described. As a result, the bone flap D is pressed against the encircling skull bone K on that side of the opening B that is diametrically opposite the first implant 200. The further implants 200', 200" serve in the present case for additional fixing in the broadest sense.

In all other respects, FIGS. 11 and 12 show that the respective supporting portions of the implants 200, 200', 200" are removed after the fixing has been completed. As a result, the implants 200, 200', 200" do not protrude upward above the skull outer side CA.

It is also evident with respect to FIG. 11 that the first contact surface 204 of the first clamping element 208 and the second contact surface 205 of the second clamping element 209 are curved. The same applies to the further implants 200', 200". Said curvature makes it possible to establish contact as far as possible over the entire surface area and thus to transfer the largest possible contact forces.

In the situation shown by means of FIG. 11, the implants 200, 200', 200" are each arranged in what is referred to as a borehole of the annular gap S. The boreholes are usually made during the trepanation and are connected to one another using a tool suitable for this. The connection of the boreholes forms the actual annular or craniotomy gap S. The radii of curvature of the contact surfaces 204, 205 are in the present case respectively matched to the radius of the borehole. The radii of curvature of the contact surfaces 204, 205 are different in different embodiments and range between 6 and 20 mm.

FIGS. 13 to 16 show variants of the implant 200 according to FIGS. 5 to 9. Their function and/or structure is largely identical to the function and the structure of the implant 200. Therefore, in order to avoid repetition, only significant differences between the variants are discussed below. Functionally identical components and/or portions are not explained separately. Instead, express reference is made to what was disclosed in relation to the implant 200.

The implant 200*a* exhibits a different shape of the clamping elements. Their end faces 211*a*, 213*a* are each provided with a profiling 225*a*. The profiling 225*a* serves to enlarge the respective contact surface area. The profiling 225*a* has a multiplicity of grooves which are elongate parallel to the longitudinal axis X and are radially inwardly recessed in the respective end face 211*a*, 213*a*. It goes without saying that a different shape of the profiling 225*a* is also conceivable. In a variant which is not shown in the figures, the profiling is formed by honeycombs, spikes or a surface that is roughened in the broadest sense.

To reduce the weight, the clamping elements of the implant 200*a* also have a respective clearance 226*a*, which can also be referred to as pocket. The clearances 226*a* are each inwardly recessed in the respective clamping element along the transverse axis Y from the end face 211*a*, 213*a*.

By contrast, the implant 200*b* according to FIG. 14 has only one clamping element 209*b*. In this variant, that edge region of the housing 215*b* that is situated opposite the second clamping element 209*b* along the transverse axis Y acts as first portion 201*b*.

The implant 200*c* according to FIG. 15 provides two mandrel portions 223*c*. The mandrel portions 223*c* project outward oppositely to one another along the transverse axis Y. The variant with two mandrel portions 223*c* is advantageous in particular when the bone flap consists of multiple, in particular fragmented segments. The segments or fragments forming the bone flap can be "put back together in jigsaw fashion", as it were, using the mandrel portions 223*c*.

In the variant according to FIG. 16, the implant 200*d* in turn has a first clamping element 208*d* and a second clamping element 209*d*. In this variant, the clamping elements 208*d*, 209*d* are manufactured from a plastically deformable mass, which is pressed laterally out of the housing of the implant 200*d* under the action of the cone element. The plastically deformable mass may be a type of putty or the like.

It goes without saying that the features of the implant 200 and the features explained with regard to the implants 200*a*, 200*b*, 200*c*, 200*d* can be combined to afford further combinations of features that are not shown in the figures.

FIGS. 17 to 29 show a further embodiment of an implant 300 according to the invention, with FIGS. 23 to 29 relating to variants of this embodiment.

The implant 300 has a longitudinal axis X, a transverse axis Y, a first portion 301, a second portion 302 and a mechanism 303. The first portion 301 is in turn designed to transfer force to the bone flap D. Accordingly, the second portion 302 is designed to transfer force to the skull bone K.

The mechanism 303 is—by contrast to the embodiments and/or variants explained above-designed for rotational displacement of the first portion 301 and of the second portion 302.

The mechanism 303 has an axis of rotation G and an eccentric element 308.

In the embodiment shown, the axis of rotation G is an axis in the geometric sense and is oriented parallel to, more specifically coaxially with, the longitudinal axis X.

The eccentric element 308 is movably mounted about the axis of rotation G and has an eccentric contour 311 with respect to the axis of rotation G. Different portions of the eccentric contour 311 form the first portion 301 and the second portion 302. A rotation of the eccentric element 308 about the axis of rotation G brings about a modification of the transverse spacing, projected onto the transverse axis Y, between the first portion 301 and the second portion 302. As a result, the eccentric element 308, more specifically its contour 311, can be clamped within the annular gap S via a rotation about the axis of rotation G, with the result that the first portion 301 is radially pressed against the bone flap D and the second portion 302 is radially pressed against the skull bone K.

Figures 17, 18, 19:
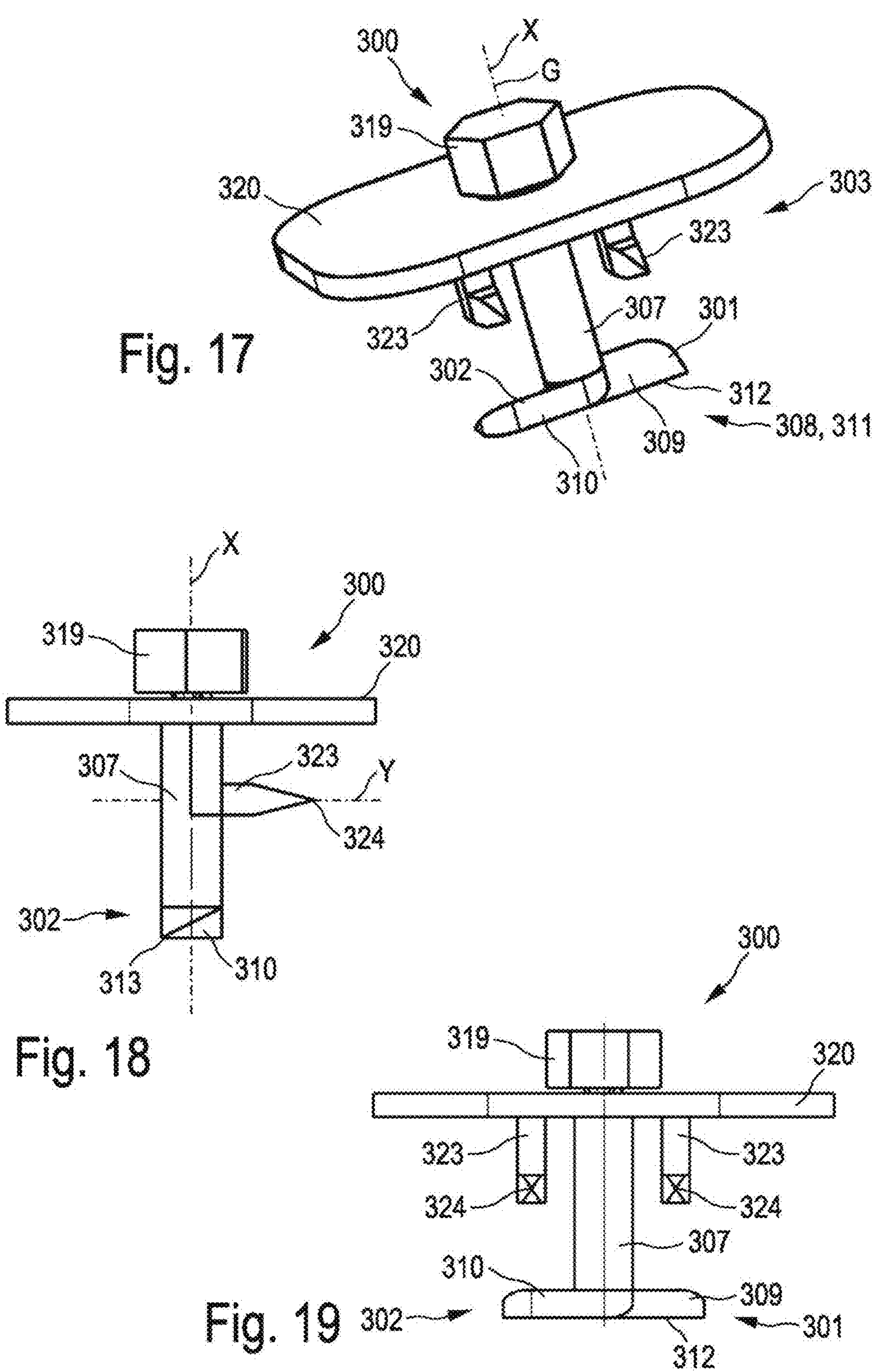
FIG. 17 shows a schematic perspective illustration of a further embodiment of an implant according to the invention.
FIG. 18 shows the implant according to FIG. 17 in a schematic side view.
FIG. 19 shows a further side view, rotated by 90°, of the implant according to FIGS. 17 and 18.

The two portions 301, 302 project outward oppositely to one another from the axis of rotation G. It goes without saying here that the shaping of the contour 311 shown in particular in FIGS. 17 to 19 is purely by way of example. The only essential thing is the eccentricity of the contour 311, i.e. that the contour 311 is not rotationally symmetrical with respect to the axis of rotation G.

In the embodiment shown, the implant 300 also has a shaft element 307, which is elongate in a straight line along the axis of rotation G between an unspecified first end and an unspecified second end. The eccentric element 308 is arranged at the second end of the shaft element 307 and fixedly connected thereto. A tool fitting element 319 is arranged at the first end and fixedly connected to the shaft element 307.

The tool fitting element 319 is designed to apply a torque directed about the axis of rotation G and in the embodiment shown is a hexagonal socket.

In the embodiment shown, the tool fitting element 319 forms an upper face end, with respect to the longitudinal axis X, of the implant 300. The eccentric element 308 forms a lower face end in this respect.

The implant 300 has a plate-like supporting portion 320 in the same way as the implant 200. The function of the supporting portion 320 is substantially similar to that of the supporting portion 220, and therefore express reference is made to what has been disclosed in this respect in order to avoid repetitions.

The implant 300 also has two mandrel portions 323, which are each provided at one end with a mandrel tip 324. At the other end, the mandrel portions 323 are each connected fixedly to the supporting portion 320. In terms of their function and configuration, the mandrel portions 323 are substantially identical to the mandrel portion 223 of the implant 200. Express reference is also made to what was said above in this respect.

The shaft element 307 is mounted on the supporting portion 320 so as to be rotatable relative thereto. In addition, the shaft element 307, together with the eccentric element 308 and the tool fitting element 319, is form-fittingly fixed relative to the longitudinal axis X on the supporting portion 320. To this end, the supporting portion 320 has an unspecified through-bore, which extends from a top side to the underside of the supporting portion 320.

In the embodiment shown, the eccentric element 308 has a first blade portion 309 and a second blade portion 310. The first blade portion 309 forms the first portion 301, as it were. The second blade portion 310 forms the second portion 302, as it were.

The first blade portion 309 in the present case has a first cutting edge 312, and the second blade portion 310 has a second cutting edge 313. The cutting edges 312, 313 are oriented oppositely to one another.

When the eccentric element 308 is being clamped in the annular gap S, the blade portions 309, 310 penetrate the respective associated bone structure, i.e. the bone flap D or the skull bone K, with their respective cutting edges 312, 313 in front. The penetration by the cutting edges 312, 313 makes it possible to achieve improved fixing.

In the embodiment shown, the tool fitting element 319 is connected to the shaft element 307 via a predetermined breaking portion 317 (see FIG. 21). The predetermined breaking portion 317 has a reduced load-bearing cross section in relation to the shaft element 307. As a result, after the fixing has been completed, the tool fitting element 319 can be sheared off of and removed from the shaft element 307 in a defined way via an additional application of torque. This avoids the implant 300 projecting excessively out of the annular gap S on the skull outer side CA. This in turn has cosmetic and medical advantages.

FIG. 22 shows an intraoperative situation using the implant 300, use being made in turn of an implant system formed of multiple implants. The implant system comprises multiple structurally identical implants 300, 300', 300". In all other respects, reference is made to the explanations given in connection with FIGS. 10 to 12 to avoid repetitions. What was explained in relation to these figures also applies, mutatis mutandis, to FIG. 22.

FIGS. 23 to 29 show different variants 300*a* to 300*f* of the implant 300. The structure and functioning of these variants is substantially identical to the implant 300. Functionally identical components and/or portions are not explained separately. Instead, express reference is made to the disclosure in relation to the implant 300.

The implant 300*a* differs in terms of the configuration of the tool fitting 319*a*. The tool fitting 319*a* is designed for fitting a screwdriver. In this respect, it is also possible to refer to a slot. By contrast to the tool fitting 319, the tool fitting 319*a* does not project beyond the supporting portion with respect to the longitudinal axis X.

The implant 300*b* according to FIG. 24 differs firstly in the absence of the mandrel portions and secondly in the configuration of the eccentric element 308*b*. In the case of the implant 300*b*, the supporting portion 320*b* has boreholes 322*b* for pre-fixing purposes. The boreholes 322*b* extend from a top side to the underside of the supporting portion 320*b*. For pre-fixing purposes, the supporting portion can be pre-fixed to the bone flap D by a screw extending through one of the bores 322*b*.

The eccentric element 308*b* has multiple first blade portions and multiple second blade portions, which are arranged one on top of another with respect to the longitudinal axis X from the second end of the shaft element in the direction toward the first end. In this respect, reference can also be made to a lower first blade 309*a*, a middle first blade 309*a'* and an upper first blade 309*a"*. Accordingly, the eccentric element 308*b* has a lower second blade 310*a*, a middle second blade 310*a'* and an upper second blade 310*a"*. It goes without saying that instead of the three blade pairs in the present case arranged one above another, there may be more or fewer blade pairs.

In the variant according to FIG. 25, only one component of the implant 300*c*, specifically its shaft element 307*c*, is illustrated. In order to avoid the shaft element 307*c*, together with the eccentric element, being unintentionally rotated back counter to the fixing direction about the axis of rotation G, the shaft element 307*c* has a thread 325*c* in the region of its first end. The thread 325*c* is screwed to a mating thread made in the supporting portion in a way which is not shown in more detail in the drawing. The mating thread may for example be in the form of a stop nut or the like.

Figure 26:
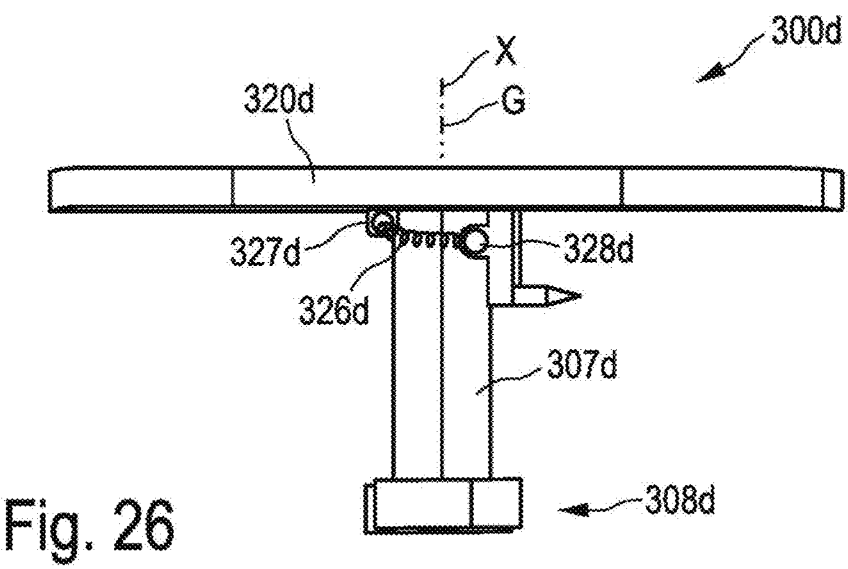
FIG. 26 shows a schematic perspective illustration of a fourth variant of the implant according to FIGS. 17 to 21.

In the variant according to FIG. 26, the implant 300*d* has, instead of a tool fitting for application of a torque, a spring element 326*d*. The spring element 326*d* is secured to a first fastening portion 327*d* at one end and to a second fastening portion 328*d* at the other end. The first fastening portion 327*d* is assigned and fixedly connected to the supporting portion 320*d*. The second fastening portion 328*d* is assigned and fixedly connected to the shaft element 307*d*. In the configuration shown by means of FIG. 26, the spring element 326*d* is biased and applies a torque, directed about the longitudinal axis X, to the shaft element 307*d*. Here, a locking device, not shown in more detail in the drawing, which keeps the shaft element 307*d* in the biased situation is present. The locking device can be transferred between a first state and a second state. In the first state of the locking device, the shaft element 307*d* is rotationally fixed relative to the supporting portion 302*d*. In the second state, the rotational movability is enabled. After the rotational movability has been enabled, the spring element 326*d* brings about a rotation of the shaft element 307*d*—and thus also of the eccentric element 308*d*—about the axis of rotation G. This clamps and/or wedges the eccentric element 308*d* in the annular gap S.

Figure 27:
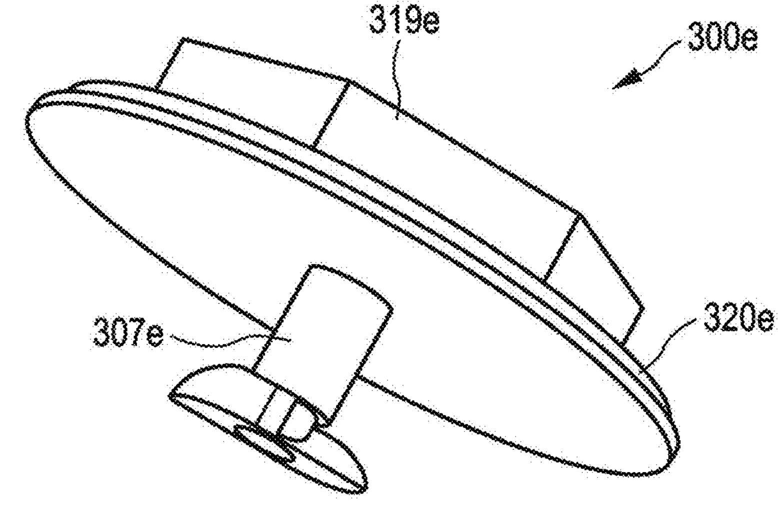
FIG. 27 shows a schematic perspective illustration of a fifth variant of the implant according to FIGS. 17 to 21.

In the variant according to FIG. 27, by contrast to the implant 300 and the previous variants 300*a* to 300*d*, the implant 300*e* has a torque-resistant connection between the supporting portion 320*e* and the shaft element 307*e*. Consequently, the supporting portion 320*e* and the shaft element 307*e* always rotate conjointly about the axis of rotation G. The supporting portion 320*e* and the shaft element 307*e* may be force-fittingly, form-fittingly and/or integrally connected to one another. A design which is cohesive in one piece is also conceivable. In the case of the implant 300*e*, the tool fitting 319*e* is arranged fixedly on a top side of the supporting portion 320*e*.

Figure 28:
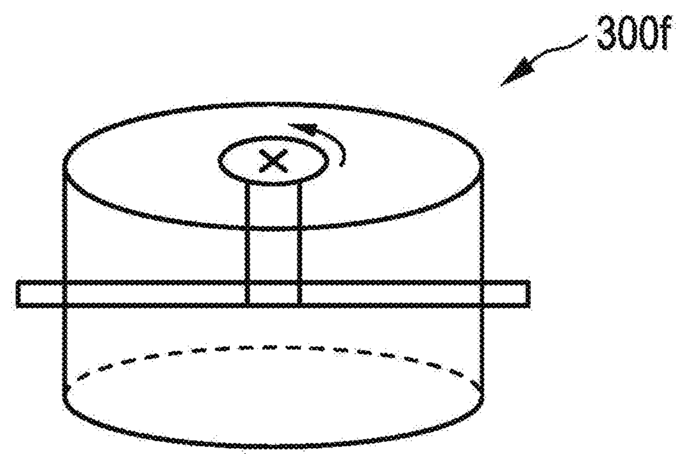
FIGS. 28, 29 show a sixth variant of the implant according to FIGS. 17 to 21 in a schematic perspective illustration (FIG. 28) and a schematic view (FIG. 29)
Figure 29:
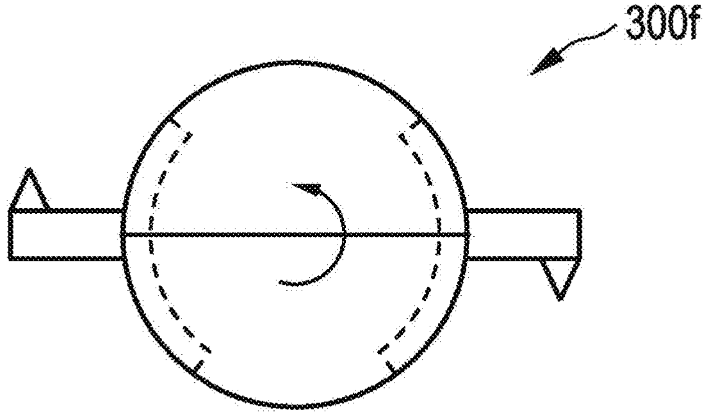

In the variant according to FIGS. 28 and 29, the implant 307*f* has a corresponding borehole design, which is based on the principle of a cavity socket.

Figure 32:
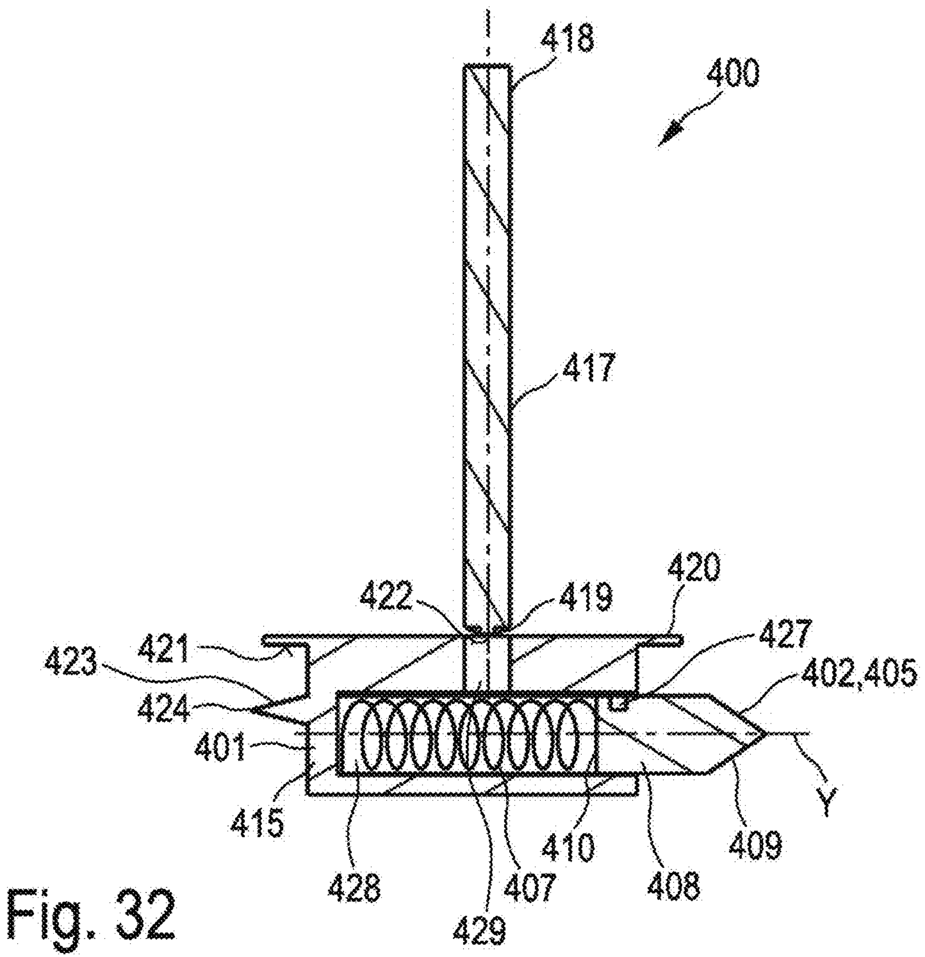
FIG. 32 shows a schematic illustration, in longitudinal section, of the implant according to FIGS. 30 and 31.
Figure 33:
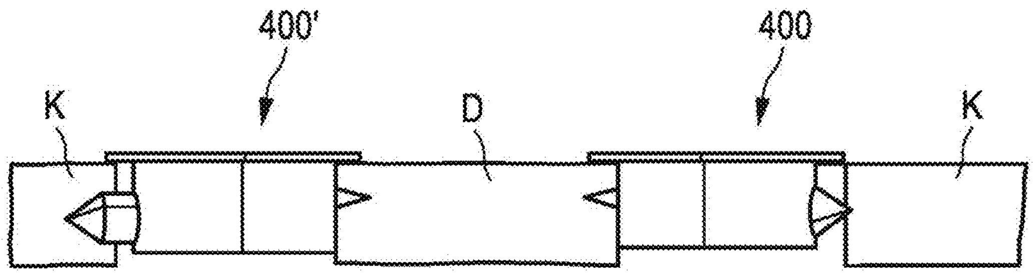
FIG. 33 shows a sectional illustration corresponding to FIG. 12 of an interoperative situation using the implant according to FIGS. 30 to 32.
Figure 34:
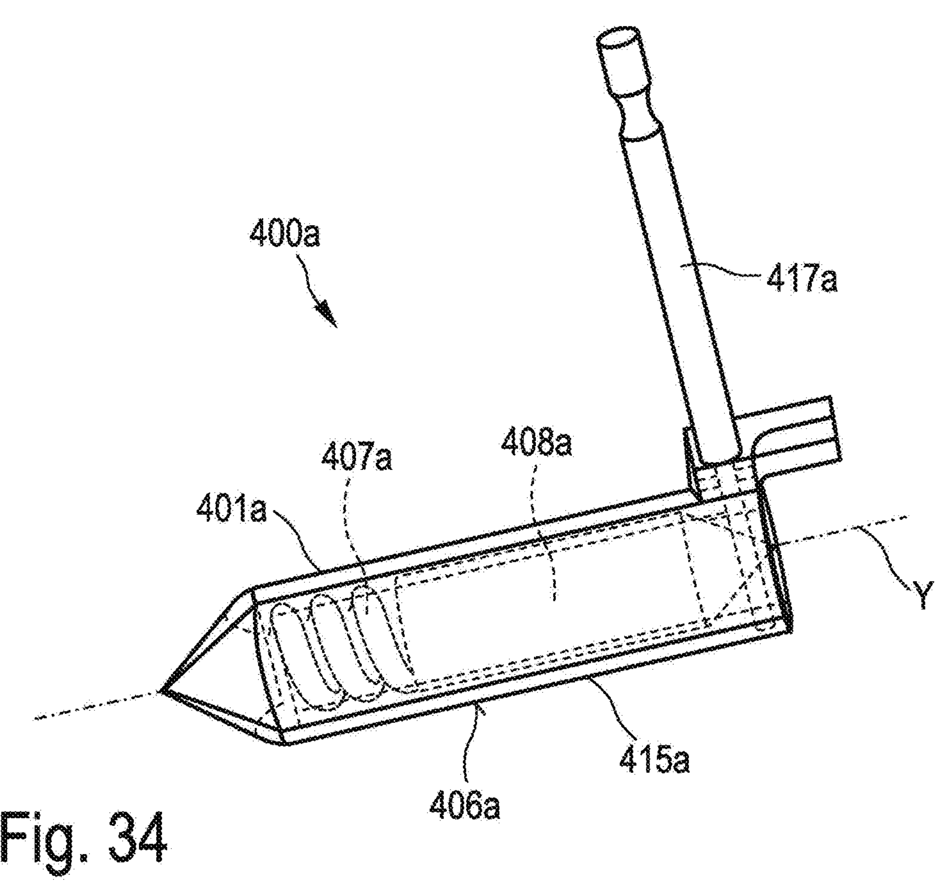
FIG. 34 shows a schematic and partially transparent perspective illustration of a first variant of the implant according to FIGS. 30 to 32.
Figure 35:
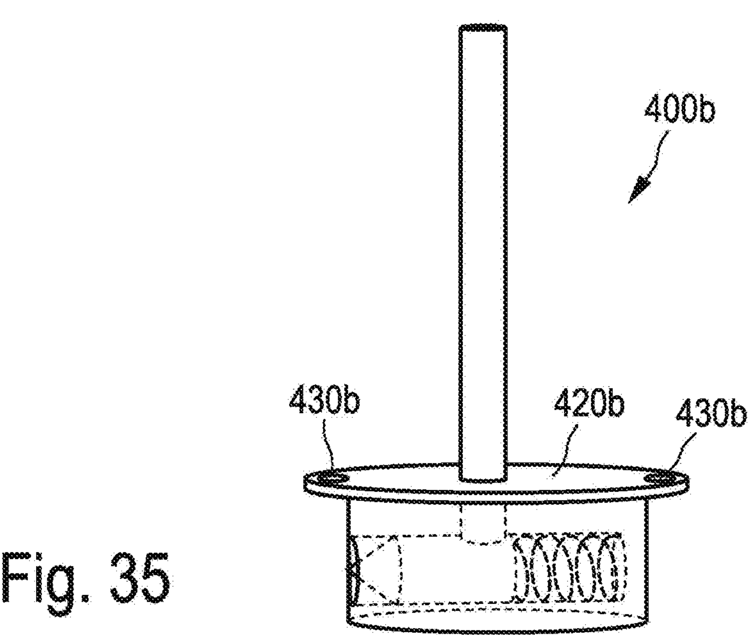
FIG. 35 shows a second variant of the implant according to FIGS. 30 to 32 in a schematic and partially transparent perspective illustration.

FIGS. 30 to 35 show a further embodiment of an implant 400 according to the invention, with FIGS. 34 and 35 relating to variants of this embodiment.

Figure 30:
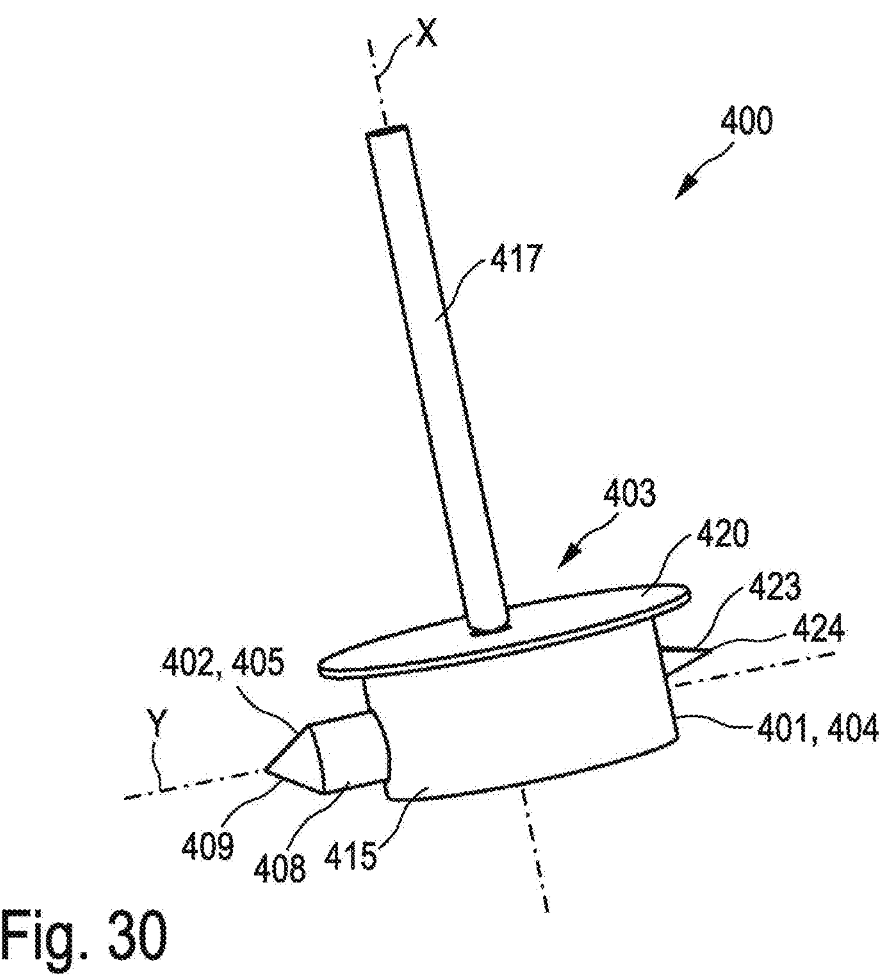
FIG. 30 shows a schematic perspective illustration of a further embodiment of an implant according to the invention.
Figure 31:
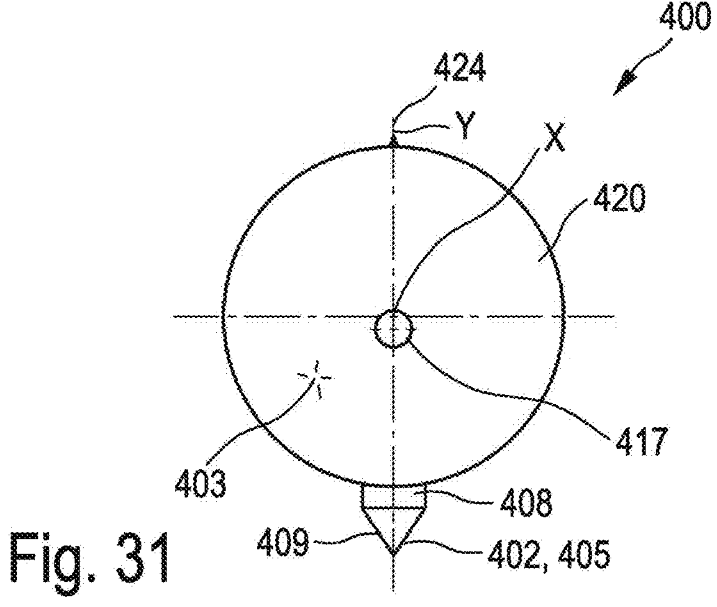
FIG. 31 shows the implant according to FIG. 30 in a schematic view.

According to FIGS. 30 to 32, the implant 400 has a longitudinal axis X, a transverse axis Y, a first portion 401, a second portion 402 and a mechanism 403.

With regard to the orientation of the longitudinal axis X and the transverse axis Y relative to the axial direction A and the radial direction R of the cranial opening B, what was said in relation to the previous embodiments applies.

The first portion 401 is in turn designed to transfer force to the bone flap D. The second portion 402 is accordingly designed to transfer force to the skull bone K. The mechanism 403 is operatively connected to the first portion 401 and to the second portion 402 in a way which will be described in more detail and makes it possible to modify the transverse spacing between these two portions.

Specifically, the mechanism has a pressure element 408 and a spring element 407.

The pressure element 408 is elongate along the transverse axis Y between a first face end 409 and a second face end 410. In addition, the pressure element 408 is movably mounted along the transverse axis Y.

The spring element 407 is supported at one end against the second portion 410 of the pressure element for force transfer. At the other end, the spring element 407 is at least indirectly operatively connected to the first portion 401. In the embodiment shown, the pressure element 408, more specifically: its first face end 409, forms the second portion 402 and/or acts as second contact surface 405.

The spring element 407 serves to bias the pressure element 408 along the transverse axis Y. The pressure element 408 is pushed outward along the transverse axis Y and with respect to the radial direction R by said biasing and in this way can be pressed against the skull bone K (see FIG. 33).

FIGS. 30 to 32 show an outer end position of the pressure element 408. In this outer end position, the pressure element 408 is displaced outward with application of force under the action of the spring element 407 along the transverse axis Y. In an inner end position, not shown in the figures, the pressure element 408 is displaced inward along the transverse axis Y, and the spring element 407 is compressed along its axial direction and thereby biased.

To lock said biasing, there is a locking element 417 in the present case. The locking element 417 can be displaced relative to the pressure element 408 between a locking position and a release position. In the locking position, the pressure element 408 is fixed with respect to the transverse axis Y by means of the locking element 417 counter to the spring force of the (biased) spring element 407. In the release position, the pressure element 408 is free to move, and therefore the spring element 407 can displace the pressure element 408 in the direction toward the outer end position.

In the embodiment shown, the locking element 417 is elongate along the longitudinal axis X between a first face end 418 and a second face end 419. The second face end 419 has a form-fitting portion 422 which form-fittingly interacts with a complementary form-fitting portion 427 of the pressure element 408 in the locking position along the transverse axis Y. In the embodiment shown, the form-fitting portion 422 is a projection which projects from the second face end 419 along the longitudinal axis X. Accordingly, the complementary form-fitting portion 427 is a recess which is made in the pressure element 408 along the longitudinal axis X. In the locking position, the projection is inserted in the recess, with the result that the pressure element 408 is form-fittingly held on the locking element 417 in the transverse direction.

For displacement into the release position, the locking element 417 is displaced axially—and with respect to the plane of the drawing in FIG. 32—upward. As a result, the form-fitting portion 422 is drawn out of the complementary form-fitting portion 427. The embodiment shown provides that the locking element 417 can be completely removed after displacement into the release position (see FIG. 33). Here, the locking element 417 is intended for manual actuation. For displacement in the direction toward the release position, the operator can grasp the locking element 417 in the region of the first face end 418 for example between the thumb and forefinger of one hand.

For pre-fixing purposes, the implant 400 has a mandrel portion 423 with a mandrel tip 424. The function and configuration of the mandrel portion 423 is substantially identical to the preceding embodiments, and therefore what was said there also applies, mutatis mutandis, in the present case.

For supporting on the skull outer side CA, a supporting portion 420 is also present. Its underside 421 is supported both on the outer side DF of the bone flap D and on the outer side KF of the skull bone for the purpose of positioning the implant 400 in the annular gap S. In all other respects, express reference is made to what was said in relation to the supporting portions 220, 320 of the preceding embodiments.

In the embodiment shown, the implant 400 also has a housing 415. The housing 415 in the present case serves in particular to receive and/or mount the spring element 407, the pressure element 408 and the locking element 417. In addition, the first portion 401 is arranged and/or formed on a side of the housing 415 diametrically opposite the first face end 409 along the transverse axis Y. Said portion of the housing 415 acts as first contact surface 404 in this respect.

The housing 415 in the present case has a first receiving clearance 428 and a second receiving clearance 429.

The first receiving clearance 428 is elongate along the transverse axis Y and serves to receive the spring element 407 and the pressure element 408. In the embodiment shown, the first receiving clearance 428 has a cylindrical, more specifically: circular-cylindrical cross section. The shaping of the pressure element 408 is matched thereto and accordingly is complementarily cylindrical, more specifically: circular-cylindrical. The first receiving clearance 428 is closed at one end and open at the other end. The pressure element 408 projects through the unspecified opening at the other end of the first receiving clearance 428. The pressure element 408 is slidingly guided along the transverse axis Y in the first receiving clearance 428. The spring element 407 is supported on an unspecified wall of the housing 415 at one end of the first receiving clearance 428. Said wall forms the first portion 401, as it were.

The second receiving clearance 429 extends into the first receiving clearance 428 from a top side of the supporting portion 420 along the longitudinal axis X. The second receiving clearance 429 serves to receive the second end 419 of the locking element 417. The locking element 417 in this respect is slidingly guided along the longitudinal axis X in the second receiving clearance 429.

The first receiving clearance 428 may also be referred to as radial bore.

The second receiving clearance 429 may also be referred to as axial bore.

In the embodiment shown, the mandrel portion 423 and the supporting portion 420 are formed in one piece on the housing 415. It goes without saying that said portions may instead also be in the form of separate components.

In the embodiment shown, the housing 415 also has a circular-cylindrical basic shape, its axial direction extending parallel to the longitudinal axis X. Owing to the circular-cylindrical configuration of the housing 415, the first portion 401 is accordingly convexly curved. This enables improved contact with the outer circumference DA of the bone flap D.

FIG. 33 shows an intraoperative situation using the implant 400, in which situation the bone flap D is already completely fixed. This is done using at least one further structurally identical implant 400'. To avoid repetition, reference is made to what was said in relation to FIG. 12.

FIGS. 34 and 35 show variants of the implant 400 according to FIGS. 30 to 33.

To avoid repetitions, only the essential differences between the implants **400*a* and 400*b* and the implant 400 will be explained below. In all other respects, express reference is made to what was said above in relation to the implant 400**.

In the variant according to FIG. 34, the implant **400*a* is designed for pre-fixing in a bore H extending radially in the outer circumference DA of the bone flap D (cf. FIG. 4**).

The first portion **401*a* accordingly has a joining surface 406*a*, which is designed for insertion in said borehole H. In this respect, reference can be made to a housing 415*a*, the cylindrical outer circumference of which forms the joining surface 406*a* and, as it were, the first portion 401*a*. The housing 415*a* in turn has unspecified receiving clearances for receiving the spring element 407*a* and the pressure element 408*a*, for the one part, and the locking element 417*a***, for the other part.

In all other respects, the locking element **417*a* is in its locking position in FIG. 34. The pressure element 408*a* is accordingly fixed in its inner end position with respect to the transverse axis Y counter to the spring force of the spring element 407***a*.

In the variant according to FIG. 35, the implant 400*b* does not have a mandrel portion. Instead, for pre-fixing purposes, through-bores 430*b* are made in the supporting portion 420*b*.

For pre-fixing purposes, the implant 400*b* is screwed to the bone flap D.

The through-bores 430*b* serve to receive the screws necessary for this.

FIGS. 36 to 45 show a further embodiment of an implant 500 according to the invention, with FIGS. 42 to 45 relating to variants thereof.

With regard to FIGS. 36 to 39, the implant 500 has a longitudinal axis X, a transverse axis Y, a first portion 501, a second portion 502 and a mechanism 503.

With regard to the orientation of the longitudinal axis X and the transverse axis Y relative to the axial direction A and the radial direction R of the cranial opening B, what was said in relation to the previous embodiments applies, mutatis mutandis.

The first portion 501 is designed to transfer force to the bone flap D.

The second portion 502 is designed to transfer force to the skull bone K encircling the cranial opening B.

The mechanism 503 operatively connected to the two portions 501, 502 is, in fundamentally the same way as the preceding embodiments, designed to enlarge the transverse spacing between the two portions 501, 502. In this respect, the two portions 501, 502 can be pressed against the bone flap D on one side and against the skull bone K on the other side by means of the mechanism 503 in this embodiment, too.

In this embodiment, the mechanism 503 has a first cylinder element 508 (FIG. 37) and a second cylinder element 509 (FIG. 38).

The first cylinder element 508 has a first longitudinal axis L1 and the second cylinder element 509 has a second longitudinal axis L2. The two longitudinal axes L1, L2 are oriented coaxially with one another and along, specifically likewise coaxially with, the transverse axis Y.

The first cylinder element 508 has a profiled first cylinder lateral surface 510 and a first surface 511. The first surface 511 forms the and/or acts as first portion 501.

The second cylinder element 509 has a profiled second cylinder lateral surface 512 and a second surface 513. The second surface 513 acts as and/or forms the second portion 502.

In the embodiment shown, the second surface 513 is a face end surface of the second cylinder element 509. This second surface is designed to radially bear against the inner circumference KI of the skull bone K. The first surface 511 is an outer lateral surface of the first cylinder element 508 and is designed for insertion into a bore H extending radially in the outer circumference DA of the bone flap D (cf. FIG. 4).

In the embodiment shown, the profiled first cylinder lateral surface 510 is an inner lateral surface of the first cylinder element 508. In the embodiment shown, the profiled second cylinder lateral surface 512 is an outer lateral surface of the second cylinder element 509. Consequently, in the embodiment shown the first cylinder element 508 is a hollow cylinder, which can also be referred to as bushing; the second cylinder element 509 can correspondingly be referred to as bolt, pin or the like. A further embodiment instead involves the reverse association, so that the first cylinder element is in the form of a bolt and the second cylinder element is in the form of a bushing.

In the ready-for-use assembled state (FIGS. 36 and 39), the first cylinder element 508 and the second cylinder element 509 are axially plug-mounted with one another. More specifically, the second cylinder element 509 is axially plugged in the first cylinder element 508. In this respect, the profiled first cylinder lateral surface 510 and the profiled second cylinder lateral surface 512 form a form-fitting and/or force-fitting connection V along the transverse axis Y (FIG. 39).

Said connection V can be established in different axial relative positions of the two cylinder elements 508, 509, as a result of which ultimately the transverse spacing between the first portion 501 and the second portion 502 can be modified.

In the embodiment shown, said connection V is a latching connection. Accordingly, the first cylinder lateral surface 510 and the second cylinder lateral surface 512 are each profiled by means of a latching geometry R1, R2, which can also be referred to as first latching geometry R1 and second latching geometry R2.

In the embodiment shown, the first latching geometry R1 has multiple circumferential grooves 514, which are at a spacing from one another along the first longitudinal axis L1 and are each recessed in the inner lateral surface of the first cylinder element 508 in the radial direction of the latter (FIG. 39).

In the embodiment shown, the second latching geometry R2 of the second cylinder element 509 has two latching projections 515 which are offset by 180° in the circumferential direction of the second cylinder element 509. Their shapes complement the circumferential grooves 514. In the present case, the latching projections 515 are arranged at an end of the second cylinder element 509 that is remote from the second surface 513.

As FIG. 39 shows, the two latching geometries R1, R2 are configured in the present case such that the latching connection V can be latched over on one side along the transverse axis Y. Consequently, in the embodiment shown the transverse spacing can only be enlarged; it cannot be reduced. In other words, the first cylinder element 508 and the second cylinder element 509 can be pulled apart, but not pushed together.

Figure 41:
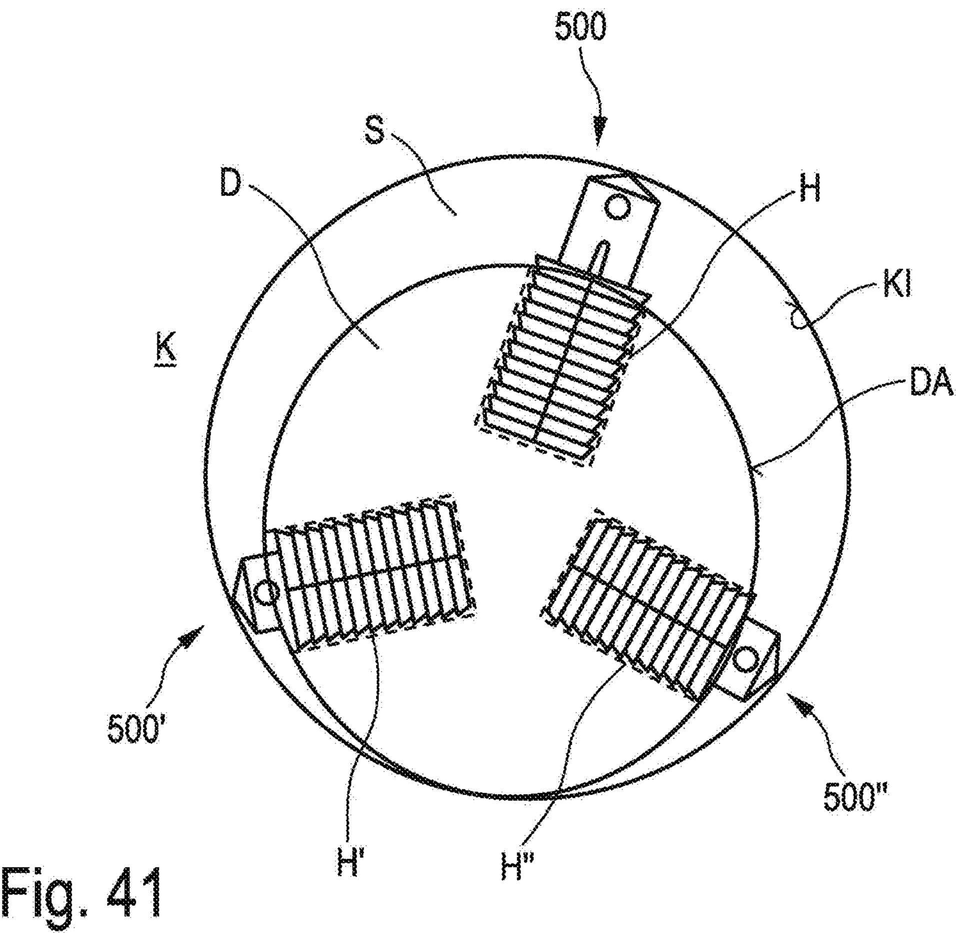
FIG. 41 shows a schematically highly simplified illustration of an intraoperative situation using the implant according to FIGS. 36 to 39.

FIG. 41 shows an intraoperative situation in which the bone flap D is fixed using the implant 500. For pre-fixing purposes, the implant 500 is firstly inserted into the bore H with the first cylinder element 508 in front. In the embodiment shown, the first cylinder element 508 on its outer lateral surface has an unspecified profiling with multiple projections 516, which are at a spacing from one another along the first longitudinal axis L1 and each extend around the circumference. These projections serve for improved pre-fixing and form a type of toothing. After the pre-fixing has been completed, the bone flap D together with the implant 500 is inserted into the opening B. Latching the latching connection V over on one side brings the second portion 502—in this case the face end surface 513 of the second cylinder element 509—to bear against the inner circumference KI of the skull bone K.

The tensile force along the transverse axis Y necessary for this is applied via a pulling eye 517 in the present case. In the present case, the pulling eye 517 is a transverse bore arranged in the region of the face end 513. To apply a tensile force to the second cylinder element 509, a tool suitable for this, for example, can be introduced into the pulling eye 517.

Figure 40:
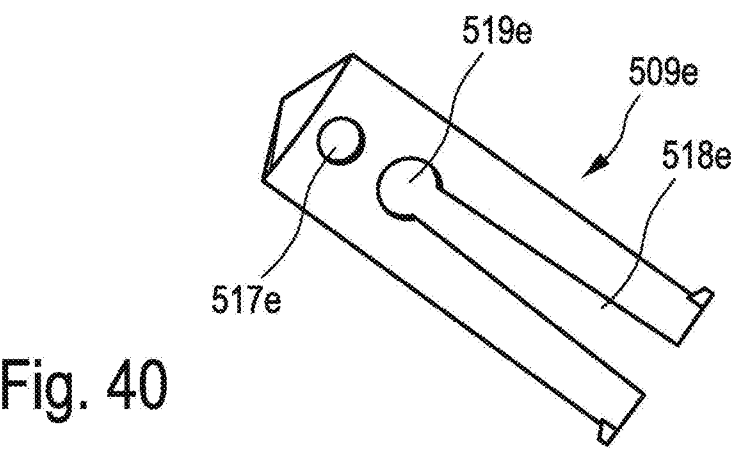
FIG. 40 shows a schematic perspective illustration of a variant of the second cylinder element according to FIG. 38.

In order to make it easier to latch over the latching connection V, in the embodiment shown the second cylinder element 509 has a longitudinal slit 518. The longitudinal slit 518 extends at one end axially into the second cylinder element 509 and enables resilient radial movability of the latching projections 515. In this respect, FIG. 40 shows a slight modification, in the case of which a second cylinder element 509*e* with a modified longitudinal slit 518*e* is provided. The longitudinal slit 518*e* has a widening 519*e* at its closed end. The widening 519*e* is arranged in the region of the pulling eye 517*e* and extends parallel thereto in similar fashion to a through-bore. The widening 519*e* assists the appropriate resilient movability of the latching projections.

With respect to FIG. 41, it also shows that the bone flap D is in turn fixed by means of multiple implants 500, 500', 500". Such fixing by means of multiple, in particular structurally identical implants is advantageous, but not imperative. In principle, it is conceivable that the bone flap D is fixed using just a single implant.

FIGS. 42 to 45 show variants of the implant 500. The function and configuration of the variants shown is substantially identical to the implant 500. To avoid repetitions, only the essential differences are discussed below. Functionally and structurally identical parts and/or portions are not explained separately. Instead, express reference is made to what was said in relation to the implant 500.

Figure 42:
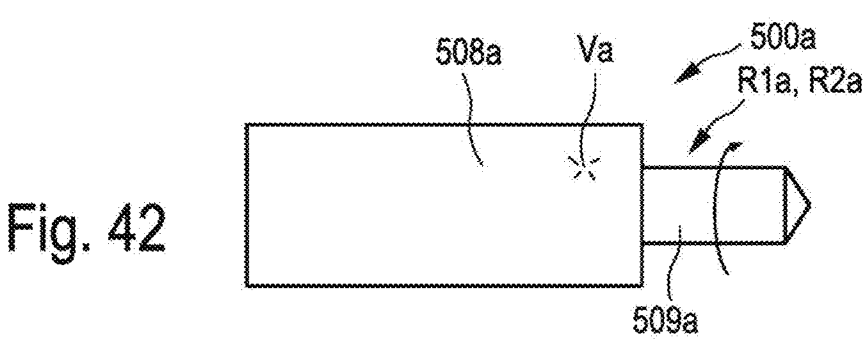
FIG. 42 shows a schematically highly simplified side view of a first variant of the implant according to FIGS. 36 to 39.

In the variant according to FIG. 42, the implant 500*a* has, instead of the latching connection V, a screwed connection Va. That is to say, the first cylinder element 508*a* and the second cylinder element 509*a* are screwed to one another for threaded movement along the transverse axis Y. To this end, the first cylinder element 508*a* has a first threaded geometry R1*a*. The second cylinder element 509*a* has a complementary second threaded geometry R2*a*. In the present case, the first threaded geometry R1*a* is an internal thread. The second threaded geometry R2*a* is an external thread.

Figure 43:
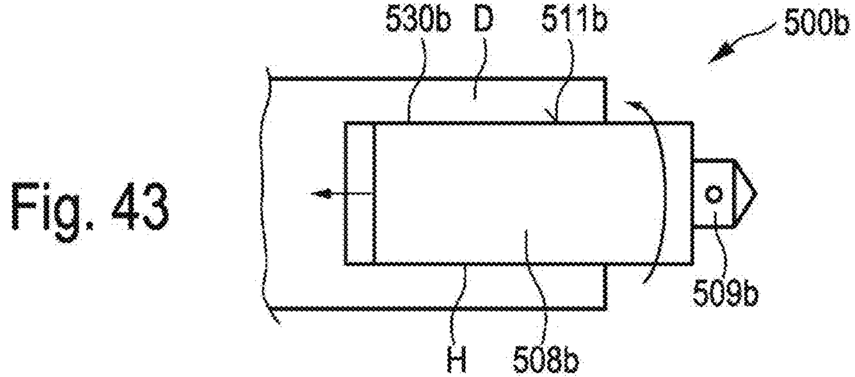
FIG. 43 shows a second variant of the implant according to FIGS. 36 to 39 in a schematically highly simplified side view.

The variant according to FIG. 43 provides that the implant 500*b* is screwed into the bore H. To this end, the outer lateral surface 511*b* has an external thread 530*b*, which is not shown in detail in the drawing. The external thread 530*b* is preferably a self-tapping and/or self-boring thread.

Figure 44:
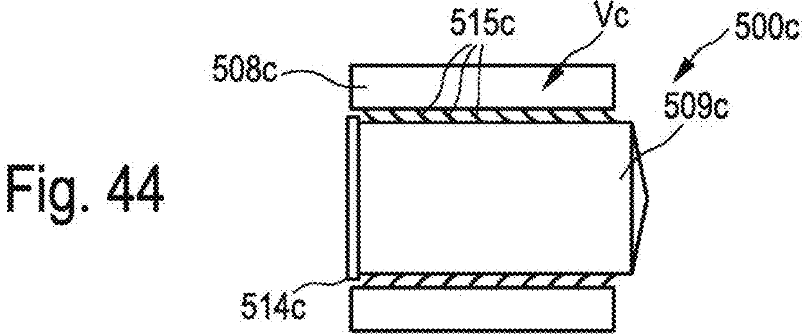
FIG. 44 shows a schematic side view of a third variant of the implant according to FIGS. 36 to 39.

In the variant according to FIG. 44, the implant 500*c* has a modified latching connection Vc. The latching connection Vc is formed between a radial collar 514*c*, arranged at the face end of the second cylinder element 509*c*, and spring elements 515*c*, arranged on the inner lateral surface of the first cylinder element 508*c*. The spring elements 515*c* are outwardly resiliently flexible in the radial direction of the cylinder elements 508*c*, 509*c*.

Figure 45:
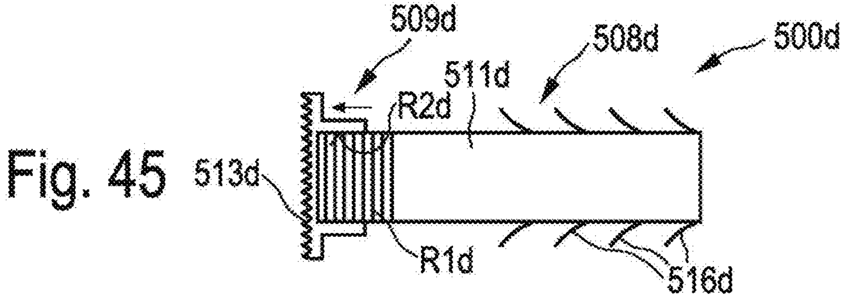
FIG. 45 shows a schematic side view of a fourth variant of the implant according to FIGS. 36 to 39.

The variant according to FIG. 45 provides—in simplified terms—the reverse assignment of the bushing geometry, for the one part, and of the bolt geometry, for the other part, on the first cylinder element 508*d* and the second cylinder element 509*d*. Accordingly, the implant 500*d* has a bolt-like first cylinder element 508*d* and a bushing-like second cylinder element 509*d*. The first cylinder element 508*d* is designed for insertion into a bore H of the bone flap D and has multiple anchoring elements 516*d* on its outer lateral surface 511*d*. The second cylinder element 509*d* is plugged at one end on the first cylinder element 508*d* and latched thereto. To this end, the outer lateral surface 511*d* at least partially has a first latching profiling R1*d*. An unspecified inner lateral surface of the second cylinder element 509*d* has a complementary second latching profiling R2*d*. The end face 513*d* of the second cylinder element 509*d* is provided with an unspecified toothing. This enables improved contact with the inner circumference KI of the skull bone.

Figure 46:
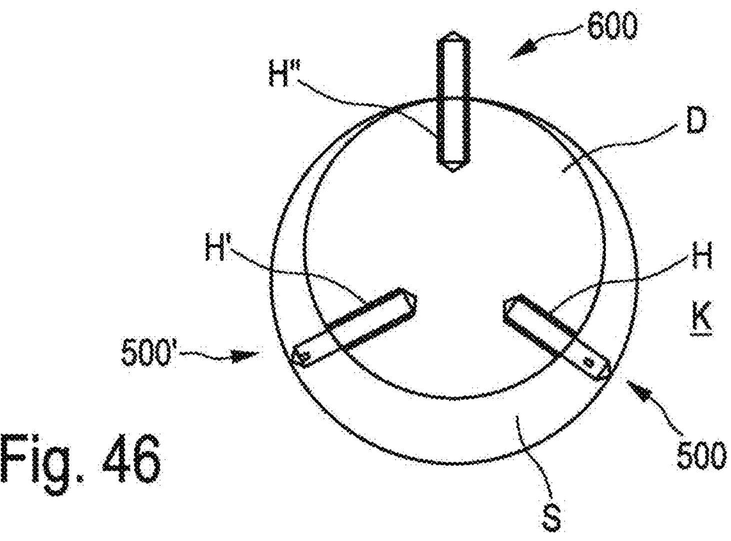
FIG. 46 shows a schematic illustration of a further intraoperative situation using the implant according to FIGS. 36 to 39 and a pin.
Figure 47:
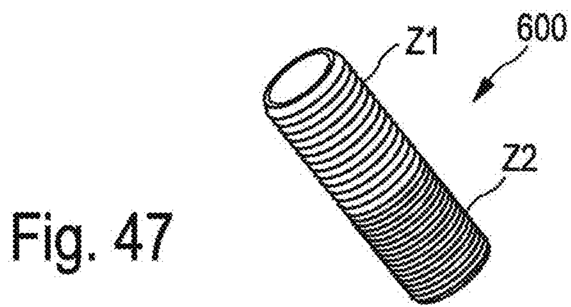
FIG. 47 shows a schematic perspective illustration of the pin according to FIG. 46.

FIG. 46 shows a further intraoperative situation, in which the bone flap D is fixed using a first implant 500, a structurally identical further implant 500' and a pin 600. The pin 600 is shown in detail in FIG. 47 and has a first toothing Z1 and a second toothing Z2 on its outer lateral surface. The first toothing Z1 serves for improved fixing of the pin in the bore H" of the bone flap D (see FIG. 46). The second toothing Z2 serves for improved anchoring of the pin 600 in an unspecified bore made in the surrounding skull bone K.

Figure 48:
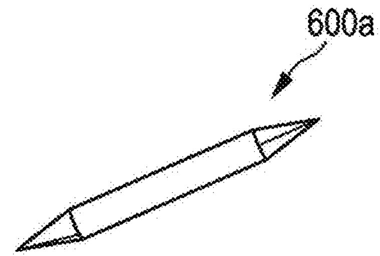
FIG. 48 shows a schematic perspective illustration of a variant of the pin according to FIG. 47.

FIG. 48 shows an alternatively configured pin 600*a*. The pin 600*a* is pointed at its axially opposite face ends. The pointed face ends make it possible to push the pin 600*a* both into an outer circumference DA of the bone flap D and into the inner circumference KI of the skull bone. This makes it possible, by contrast to the pin 600, to do away with making bores in the skull bone K and/or the bone flap D.

The invention claimed is:

1. An implant for fixing a cranial bone flap in a cranial opening, the implant comprising:

a longitudinal axis configured to align along an axial direction of the cranial opening;

a transverse axis configured to align along a radial direction of the cranial opening;

a first portion designed to transfer force to the cranial bone flap;

a second portion designed to transfer force to a skull bone encircling the cranial opening; and a mechanism operatively connected to the first portion and the second portion, the mechanism being configured such that a transverse spacing, projected onto the transverse axis, between the first portion and the second portion, is enlargeable, such that the first portion is pressable radially inwardly against the cranial bone flap, and such that the second portion is pressable radially outwardly against the skull bone, the first portion and/or the second portion being designed for arrangement in an annular gap formed between an outer circumference of the cranial bone flap and an inner circumference of the skull bone, and wherein the mechanism has at least one clamping element and a cone element, wherein the at least one clamping element is movably mounted along the transverse axis and has an inner cone surface and an end face forming the first portion or the second portion, wherein the cone element is movably mounted along the longitudinal axis and has an outer cone surface interacting with the inner cone surface, and wherein the at least one clamping element is displaceable by a movement of the cone element along the transverse axis.

2. The implant, according to claim 1, wherein the mechanism is designed for translational displacement of the first portion and/or of the second portion along the transverse axis.

3. The implant according to claim 1, wherein the first portion has a first contact surface designed to radially bear against the outer circumference of the cranial bone flap, and/or the second portion has a second contact surface designed to radially bear against the inner circumference of the skull bone.

4. The implant according to claim 1, wherein a supporting portion is arranged above the first portion and the second portion along a longitudinal axis, the supporting portion having an underside designed for supporting on a first outer side of the skull bone and a second outer side of the cranial bone flap.

5. The implant according to claim 4, wherein the supporting portion is connected to the implant by a detachable joining connection.

6. The implant according to claim 1, further comprising at least one mandrel portion that is elongate along the transverse axis and at one end has a mandrel tip projecting beyond the first portion, the mandrel tip designed to radially pierce into the outer circumference of the cranial bone flap.

7. The implant according to claim 1, wherein the mechanism has a further clamping element that is oppositely displaceable by the movement of the cone element along the transverse axis.

8. The implant according to claim 1, wherein the cone element has a thread screwed to a complementary mating thread for threaded movement along the longitudinal axis.

9. An implant system comprising:

at least two implants according to claim 1.

10. An implant for fixing a cranial bone flap in a cranial opening, the implant comprising:

a housing having a longitudinal axis configured to align along an axial direction of the cranial opening, and a transverse axis configured to align along a radial direction of the cranial opening;

a first portion slidingly mounted in the housing to move along the transverse axis and having a respective convex semicircular contact surface, as viewed along the longitudinal axis, facing away from the housing and designed to transfer force to the cranial bone flap;

a second portion slidingly mounted in the housing to move along the transverse axis and having a respective convex semicircular contact surface, as viewed along the longitudinal axis, facing away from the housing and designed to transfer force to a skull bone encircling the cranial opening; and a mechanism operatively connected to the housing, the first portion and the second portion, the mechanism being configured such that a transverse spacing, projected onto the transverse axis, between the first portion and the second portion, is enlargeable, such that the first portion is pressable radially inwardly against the cranial bone flap, and such that the second portion is pressable radially outwardly against the skull bone, and the first portion and/or the second portion being designed for arrangement in an annular gap formed between an outer circumference of the cranial bone flap and an inner circumference of the skull bone.

* * * * *